(12) United States Patent
Shen et al.

(10) Patent No.: US 10,093,679 B2
(45) Date of Patent: Oct. 9, 2018

(54) AMINO SULFONYL-BASED COMPOUNDS, THE PREPARATION METHOD THEREFOR AND USE THEREOF

(71) Applicants: SUZHOU VIGONVITA LIFE SCIENCES CO., LTD., Jiangsu (CN); SHANGHAI INSTITUTE OF MATERIA MEDICA, CHINESE ACADEMY OF SCIENCES, Shanghai (CN); TOPHARMAN SHANGHAI CO., LTD., Shanghai (CN)

(72) Inventors: Jingshan Shen, Shanghai (CN); Zheng Liu, Shanghai (CN); Zhen Wang, Shanghai (CN); Guanghui Tian, Jiangsu (CN); Jianfeng Li, Shanghai (CN); Xiaojun Yang, Shanghai (CN)

(73) Assignees: SUZHOU VIGONVITA LIFE SCIENCES CO., LTD, Suzhou (CN); SHANGHAI INSTITUTE OF MATERIA MEDICA, CHINESE ACADEMY OF SCIENCES, Shanghai (CN); TOPHARMAN SHANGHAI CO., LTD, Shanghai (CN)

( * ) Notice: Subject to any disclaimer, the term of this patent is extended or adjusted under 35 U.S.C. 154(b) by 0 days.

(21) Appl. No.: 15/509,796

(22) PCT Filed: Sep. 11, 2015

(86) PCT No.: PCT/CN2015/089471
§ 371 (c)(1),
(2) Date: Mar. 8, 2017

(87) PCT Pub. No.: WO2016/037592
PCT Pub. Date: Mar. 17, 2016

(65) Prior Publication Data
US 2017/0298080 A1   Oct. 19, 2017

(30) Foreign Application Priority Data
Sep. 12, 2014 (CN) .......................... 2014 1 0466628

(51) Int. Cl.
| | | |
|---|---|---|
| C07D 261/20 | (2006.01) | |
| C07D 495/04 | (2006.01) | |
| A61K 31/33 | (2006.01) | |
| A61K 31/381 | (2006.01) | |
| C07D 209/14 | (2006.01) | |
| C07D 307/77 | (2006.01) | |
| C07D 231/56 | (2006.01) | |
| C07D 275/04 | (2006.01) | |
| C07D 333/20 | (2006.01) | |
| A61K 31/415 | (2006.01) | |
| A61K 31/42 | (2006.01) | |
| A61K 31/425 | (2006.01) | |
| C07D 333/46 | (2006.01) | |

(52) U.S. Cl.
CPC ............ *C07D 495/04* (2013.01); *A61K 31/33* (2013.01); *A61K 31/381* (2013.01); *A61K 31/415* (2013.01); *A61K 31/42* (2013.01); *A61K 31/425* (2013.01); *C07D 209/14* (2013.01); *C07D 231/56* (2013.01); *C07D 261/20* (2013.01); *C07D 275/04* (2013.01); *C07D 307/77* (2013.01); *C07D 333/20* (2013.01); *C07D 333/46* (2013.01)

(58) Field of Classification Search
CPC .................................................... C07D 261/20
See application file for complete search history.

(56) References Cited

FOREIGN PATENT DOCUMENTS

CN          101090896          12/2007

OTHER PUBLICATIONS

International Search Report, International Preliminary Report on Patentability and Written Opinion, issued in International Patent Application No. PCT/CN2015/089471, dated Dec. 15, 2015.
Parker, M. H., et al., "Novel, Broad-Spectrum Anticonvulsants Containing a Sulfamide Group: Advancement of N-((Benzo[b]thien-3-yl)methyl)sulfamide (JNJ-26990990) into Human Clinical Studies," Journal of Medicinal Chemistry, vol. 52, No. 23, Apr. 2009, pp. 7528-7536.
Lee, J .S., et al., "Intramolecular Sulfamylation Reaction of N-(1H-indol-3-yl)ethylsulfamides: Synthesis of 2,3,4,9-Tetrahydro-1,2-thiazino[5, 6-b]indole 1,1-Dioxides," Bull Korean Chemistry Society, vol. 24, No. 9, Dec. 2003, pp. 1399-1402.
(Continued)

*Primary Examiner* — Shawquia Jackson
(74) *Attorney, Agent, or Firm* — Ping Wang; Morris, Manning & Martin, LLP

(57) ABSTRACT

Disclosed are aminosulfonyl-based compounds represented by the general formula I or tautomers, enantiomers, racemates or pharmaceutically acceptable salts thereof, a method for preparing the same, pharmaceutical compositions and uses thereof. The compounds can be used to treat epilepsy, convulsions, obesity and the like.

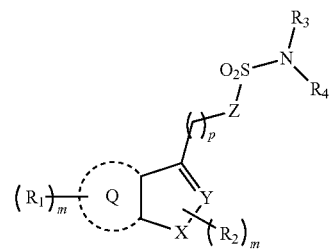

7 Claims, No Drawings

(56) References Cited

OTHER PUBLICATIONS

Soledade, M., et al., "Toward the Control of Leptosphaeria Maculans: Design, Syntheses, Biological Activity, and Metabolism of Potential Detoxification Inhibitors of the Crucifer Phytoalexin Brassinin," Bioorganic & Medicinal Chemistry, vol. 14, Apr. 2006, pp. 4958-4979.

AMINO SULFONYL-BASED COMPOUNDS, THE PREPARATION METHOD THEREFOR AND USE THEREOF

This application is a national stage application of Chinese Patent Application No. PCT/CN2015/089471, filed Sep. 11, 2015. The entirety of the aforementioned application is incorporated herein by reference.

FIELD

The present invention belongs to the field of pharmaceutical chemistry. In particular, the present invention relates to a novel aminosulfonyl-based compounds represented by the general formula I or tautomers, enantiomers, racemates or a pharmaceutically acceptable salts thereof, a method for preparing the same, pharmaceutical compositions comprising the same and uses thereof.

BACKGROUND

Epilepsy is the second most common neurological disease after stroke, and seriously threatens human health and it is a chronic disease of short brain dysfunction caused by sudden abnormal discharge of cerebral neuron. Clinical manifestation of epilepsy is epileptic seizure which is mainly divided into two categories, generalized and partial seizures, wherein the partial seizures accounted for 60% of the epileptic seizures. Generalized seizures shows sign of loss of consciousness including generalized tonic clonic seizure (grand mal seizures), absence seizure (petit mal epilepsy), etc. Partial seizures generally do not appear disturbance of consciousness and includes simple partial seizures, autonomic nervous seizures and complex partial seizures etc.

According to statistics, epileptic patients account for about 1% of the world's population, wherein symptoms of 75%-80% of patients can be effectively controlled by conventional drugs such as phenytoin, zonisamide, topiramate, etc. However, there are still about 20%-25% of patients who fail to respond to drug therapy, which prompted us to continue to develop new antiepileptic drugs.

SUMMARY OF THE INVENTION

Technical Problem

One object of present invention is to provide aminosulfonyl-based compounds represented by the general formula I or tautomers, enantiomers, racemates or pharmaceutically acceptable salts thereof.

Another object of present invention is to provide a method for preparing the compounds of present invention.

Yet object of present invention is to provide a use of aminosulfonyl-based compounds represented by the general formula I or tautomers, enantiomers, racemates or a pharmaceutically acceptable salts thereof as antiepileptic, anticonvulsant, slimming drugs etc, and a use thereof in preparing medicine for treating epilepsy, convulsions, obesity, etc.

Another object of present invention is to provide pharmaceutical compositions comprising one or more selected from the group consisting of aminosulfonyl-based compounds represented by the general formula I or tautomers, enantiomers, racemates or pharmaceutically acceptable salts thereof.

Yet object of present invention is to provide therapeutic method for treating epilepsy, convulsions, obesity.

DETAILED DESCRIPTION

Technical Solution

According to one aspect of present invention, it provides aminosulfonyl-based compounds represented by the general formula I or tautomers, enantiomers, racemates or a pharmaceutically acceptable salts thereof.

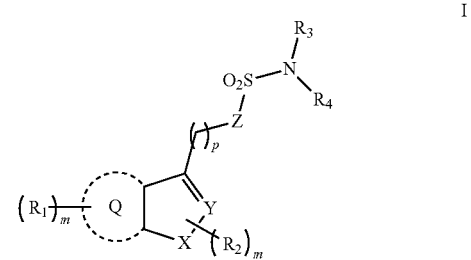

X is O, S, NH or $CH_2$,

Y is N or CH; when X is O or S and Q is benzene ring, Y is not CH;

Z is N—$R_5$, O or $CHR_5$; when X is O and Y is N, Z is not O or $CH_2$;

Q ring is a 6- to 10-membered aromatic ring, or 5- or 6-membered heterocyclic ring or a heteroaromatic ring containing 1 to 4 heteroatoms selected from N, O and S, or Q ring does not exist; preferably, Q ring is a benzene ring, 5- to 6-membered heterocyclic or heteroaromatic ring containing 1 to 2 heteroatoms selected from N, O and S, or Q ring does not exist; more preferably, Q ring is a benzene ring or a thiophene ring;

m is an integer of 0 to 4, preferably m is 0, 1 or 2;

n is an integer of 0 to 2, preferably n is 0 or 1;

p is an integer of 1 to 2;

$R_1$s are each independently hydrogen, amino, halogen, trifluoromethyl, hydroxy, nitro, nitrile, mercapto, carboxyl, aldehyde group, oxo(=O) group, thio(=S) group, C1~C10 alkyl, C2~C10 alkenyl, C2~C10 alkynyl, C3~C10 cycloalkyl, C1~C10 alkoxyl, C1~C10 alkylacyl (i.e., —C(O)—C1~C10 alkyl), C1~C10 alkoxyl carbonyl (i.e., —C(O)O—C1~C10 alkyl), C1~C10 alkylacyloxy (i.e., —OC(O)—C1~C10 alkyl), —$NR_6R_7$, —$CONR_6R_7$, —$OCONR_6R_7$, C1~C10 thioalkyl, sulfonic acid group, aminoformyl(—$CONH_2$), sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S; in which the amino, C1~C10 alkoxy, C1~C10 alkyl, C1~C10 alkyl acyl, C1~C10 alkoxyl carbonyl, C1~C10 alkyl acyloxy, sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S may be optionally substituted by one or more substituents selected from a group consisting of halogen, trifluoromethyl, hydroxyl, nitro, amino, cyano, carboxyl, aldehyde group, C1~C10 alkyl, C1~C10 alkoxyl, C1~C10 alkyl acyloxy, C1~C10 alkoxyl carbonyl, C1~C10 alkyl acyl, sulfonyl, C1~C10 alkyl sufonyl, phenyl, and benzyl;

R$_2$s are each independently hydrogen, amino, halogen, trifluoromethyl, hydroxyl, nitro, cyano, mercapto group, carboxyl, aldehyde group, C1~C10 alkyl, C2~C10 alkenyl, C2~C10 alkynyl, C3~C10 cycloalkyl, C1~C10 alkoxyl, C1~C10 alkyl acyl (i.e., —C(O)—C1~C10 alkyl), C1~C10 alkoxyl carbonyl (i.e., —C(O)(O)—C1~C10 alkyl), C1~C10 alkyl acyloxy (i.e., —(O)C(O)—C1~C10 alkyl), —NR$_6$R$_7$, —CONR$_6$R$_7$, —OCONR$_6$R$_7$, C1~C10 thioalkyl, sulfonic acid group, amino formyl (—CONH$_2$), sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S; the amino, C1~C10 alkoxy, C1~C10 alkyl, C1~C10 alkyl acyl, C1~C10 alkoxyl carbonyl, C1~C10 alkyl acyloxy, sulfonyl, C6~C10 aryl, 4-~10-membered heterocyclic group or 4-~10-membered heteroaryl may be optionally substituted by one or more substituents selected from a group consisting of halogen, trifluoromethyl, hydroxyl, nitro, amino, cyano, carboxyl, aldehyde group, C1~C10 alkyl, C1~C10 alkoxyl, C1~C10 alkyl acyloxy, C1~C10 alkoyxl acyl, C1~C10 alkyl acyl, sulfonyl, C1~C10 alkyl sulfonyl, phenyl, and benzyl;

R$_3$ and R$_4$ are each independently hydrogen, amino, trofluoromethyl, hydroxyl, carboxyl, aldehyde group, amino, C1~C10 alkyl, C2~C10 alkenyl, C2~C10 alkynyl, C3~C10 cycloalkyl, C1~C10 alkoxyl, C1~C10 alkoxyl carbonyl (i.e., —C(O)(O)—C1~C10 alkyl), C1~C10 alkyl acyl (i.e., —C(O)—C1~C10 alkyl), C1~C10 alkyl acyloxy (i.e., —OC(O)—C1~C10 alkyl), sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S; in which the amino, C1~C10 alkyl, C1~C10 alkoxy, C1~C10 alkoxyl carbonyl, C1~C10 alkyl acyl, C1~C10 alkyl acyloxy, sulfonyl, C6~C10 aryl, 4-~10-membered heterocyclic group containing 1 to 4 heteroatoms selected from a group consisting of N, O and S, or 4-~10-membered heteroaryl containing 1 to 4 heteroatoms selected from a group consisting of N, O and S may be optionally substituted by one or more substituents selected from a group consisting of halogen, trifluoromethyl, hydroxyl, nitro, amino, cyano, carboxyl, aldehyde group, C1~C10 alkyl, C1~C10 alkoxyl, C1~C10 alkyl acyloxy, C1~C10 alkoxyl carbonyl, C1~C10 alkyl acyl, sulfonyl, C1~C10 alkyl sulfonyl, phenyl and benzyl;

or R$_3$, R$_4$ together with the N atom to which they are bonded form a 4- to 8-membered heterocyclic group containing 1 to 4 heteroatoms selected from a group consisting of N, S, O or 4- to 8-membered heteroaryl containing 1 to 4 heteroatoms;

R$_5$ is H or C1~C10 alkyl;

R$_6$ and R$_7$ are each independently H or C1~C10 alkyl, or R$_6$ and R$_7$ together with the N atom to which they are bonded form a 4-~8-membered heterocyclic group containing 1~4 heteroatoms selected from a group consisting of N, S and O, or form 4-~8-membered heteroaryl containing 1~4 heteroatoms; preferably, R$_6$ and R$_7$ are each independently H or methyl.

Preferably, in the structure of the compounds represented by general formula I, the

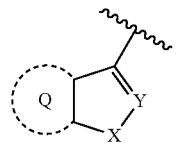

ring has the following structure:

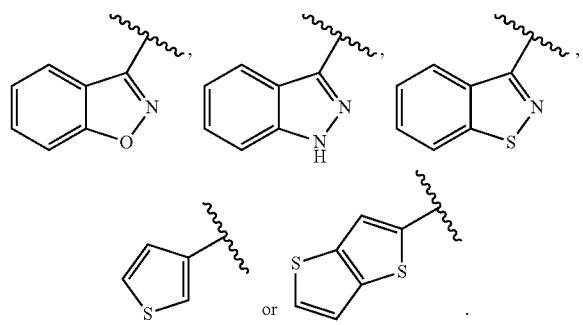

More preferably, the compounds represented by general formula I have the following structure IA

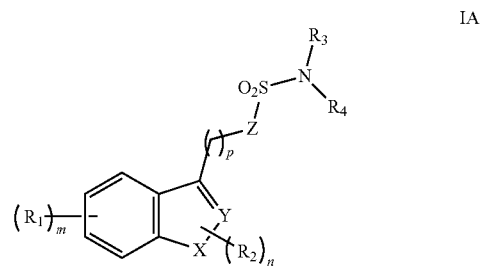

wherein, X is O, S or NH;

Z, m, n, p, R$_1$, R$_2$, R$_3$ and R$_4$ are same as defined above.

More preferably,

Z is O or N—R$_5$;

m is 0, 1 or 2;

n is 0 or 1;

p is 1;

R$_1$s are each independently hydrogen, halogen, trifluoromethyl, hydroxyl, nitro, cyano, mercapto, carboxyl, aldehyde group, C1~C8 alkyl, C2~C8 alkenyl, C2~C8 alkynyl, C3~C8 cycloakyl, C1~C8 alkoxyl, C1~C8 alkyl acyl (i.e., —C(O)—C1~C8 alkyl), C1~C8 alkoxy acyl (i.e., —C(O)(O)—C1~C8 alkyl), C1~C8 alkyl acyloxy(i.e., —(O)C(O)—C1~C8 alkyl), —NR$_6$R$_7$, —CONR$_6$R$_7$, —OCONR$_6$R$_7$, C1~C8 thioalkyl, sulfonamido, aminoformyl(—CONH$_2$), sulfonyl, C1~C8 alkylsulfonyl, C6~C10 aryl, 4~10~membered heterocyclic group or 4-~10-membered heteroaryl containing 1~3 heteroatoms selected from a group consisting of N, O and S;

R$_2$s are each independently hydrogen, halogen, trifluoromethyl, hydroxyl, nitro, cyano, amino, mercapto, carboxyl, aldehyde group, C1~C8 alkyl, C2~C8 alkenyl, C2~C8 alkynyl, C3~C8 cycloakyl, C1~C8 alkoxyl, C1~C8 alkyl acyl (i.e., —C(O)—C1~C8 alkyl), C1~C8 alkoxy acyl (i.e., —C(O)(O)—C1~C8 alkyl), C1~C8 alkyl acyloxy(i.e., —(O)C(O)—C1~C8 alkyl), —NR$_6$R$_7$, —CONR$_6$R$_7$, —OCONR$_6$R$_7$, C1~C8 thioalkyl, sulfonic acid group, sulfonamido, aminoformyl(—CONH$_2$), sulfonyl, C1~C8 alkylsulfonyl, C6~C10 aryl, 4-~10-membered heterocyclic group containing 1~3 heteroatoms selected from a group consisting of N, O and S or 4-~10-membered heteroaryl containing 1~3 heteroatoms selected from a group consisting of N, O and S;

R$_3$ and R$_4$ are each independently H or C1~C8 alkyl or 5-~6-membered heteroaryl; or R$_3$ and R$_4$ together with the N atom to which they are bonded form 5-~7-membered heterocyclic ring group containing 1~3 heteroatoms selected from a group consisting of N, S and O or 5-~7-membered heteroaryl containing 1~3 heteroatoms selected from a group consisting of N, S and O, for example, including, but not limit to, pyrrolidinyl, imidazolyl, piperazinyl, piperidinyl, morpholinyl;

R$_5$ is H or C1~C3 alkyl;

R$_6$ and R$_7$ are each independently H or C1~C8 alkyl;

or R$_6$ and R$_7$ together with the N atom to which they are bonded form a 5- to 7-membered heterocyclic group containing 1 to 3 heteroatoms selected from a group consisting of N, S and O or 5- to 7-membered heteroaryl containing 1 to 3 heteroatoms selected from a group consisting of N, S and O.

More preferably, the compounds represented by general formula I have the following structure:

wherein, X is O, S or NH;

Y is N or CH; and when X is O or S, Y is not CH;

Z is O or N—R$_5$; and when X is O and Y is N, Z is not O or CH$_2$;

Q is benzene ring;

m is 0, 1 or 2;

n is 0 or 1;

p is 1;

R$_1$ is H, F, Cl, NO$_2$, NH$_2$, NHCOCH$_3$ or methoxyl;

R$_2$ is H or methyl;

R$_3$ and R$_4$ are each independently H, methyl, ethyl, or imidazolyl;

R$_5$ is H;

R$_6$ and R$_7$ are each independently H or methyl.

Most preferably, the compounds represented by general formula I are the following compounds:

N-[(6-chloro-benzo[d]isoxazol-3-yl)methyl]-sulfamide;
N-[(6-fluoro-benzo[d]isoxazol-3-yl)methyl]-sulfamide;
N-[(benzo[d]isoxazol-3-yl)methyl]-sulfamide;
N-[(benzo[d]isothiazol-3-yl)methyl]-sulfamide;
N-[(benzo[d]isoxazol-3-yl)methyl]-N'-methyl-sulfamide;
N-[(benzo[d]isoxazol-3-yl)methyl]-N',N'-dimethyl-sulfamide;
benzo[d]isothiazol-3-ylmethyl sulfamate;
N-[(6-fluoro-benzopyrazol-3-yl)methyl]-sulfamide;
N-[(5-methoxyl-benzo[d]isoxazol-3-yl)methyl]-sulfamide;
N-[(5-nitro-benzo[d]isoxazol-3-yl)methyl]-sulfamide;
N-[(5-chloro-benzo[d]isoxazol-3-yl)methyl]-sulfamide;
N-[(thiophen-3-yl)methyl]-sulfamide;
N-[(thieno[3,2-b]thiophen-3-yl)methyl]-sulfamide;
N-[(2-chloro-thiophen-3-yl)methyl]-sulfamide.

In present invention, the terms used are defined as follows:

Halogen generally refers to fluorine, chlorine, bromine or iodine; preferably fluorine, chlorine or bromine; more preferably fluorine or chlorine;

C1 to C10 alkyl refers to a straight or branched saturated hydrocarbon group containing 1 to 10 carbon atoms, for example, methyl, ethyl, n-propyl, isopropyl, n-butyl, isobutyl, sec-butyl, tert-butyl, n-pentyl, 1-ethylpropyl, isopentyl, neopentyl, isohexyl, 3-methylpentyl or n-hexyl, etc, preferably methyl, ethyl, n-propyl, isopropyl, butyl, isobutyl or tert-butyl; similarly, the C1-C8 alkyl group refers to a straight or branched saturated hydrocarbon radical containing from 1 to 8 carbon atoms;

C3-C10 cycloalkyl refers to a saturated cycloalkyl having 3 to 10 carbon atoms, such as cyclopropyl, cyclobutyl, cyclopentyl, cyclohexyl, cycloheptyl or cyclooctyl et al.

The aromatic ring is an aromatic ring, for example, a benzene ring; the heteroaromatic ring is an aromatic ring containing at least one heteroatom selected from a group consisting of O, S or N, such as thiazole ring, pyrazole ring, pyridine ring or imidazole ring.

The compounds of present invention represented by general formula I also include tautomers, enantiomers, racemates or pharmaceutically acceptable salts thereof.

The present invention provides pharmaceutically acceptable salts of compounds represented by general formula I, for example, non-toxic acid addition salts formed with inorganic acids such as hydrochloric acid, hydrobromic acid, hydroiodic acid, sulfuric acid and phosphoric acid; organic carboxylic acids or organic sulfonic acids; preferably phosphoric acid, malic acid, lactic acid, maleic acid, hydrochloric acid, methanesulfonic acid, sulfuric acid, citric acid, tartaric acid, acetic acid or trifluoroacetic acid, more preferably the non-toxic acid addition salts may be phosphates, methanesulfonates, or trifluoroacetate. The compounds represented by general formula I may further react with alkalines to form metal salts thereof, especially, non-toxic metal salts, for example sodium salts and potassium salts.

The compounds represented by general formula I may contain one or more chiral centers so that the compounds may have stereoisomers, i.e., enantiomers, diastereomers or mixtures thereof. If the compounds represented by the general formula I contain alkenyl or alkenylene, cis (E) and trans (Z) isomerization may also be present. Thus, the compounds represented by general formula I of the present invention may be a single isomer or a mixture of isomers.

The separation of diastereoisomers or cis and trans isomers can be performed by conventional techniques, such as fractional crystallization of mixture of stereoisomers of compounds represented by general formula I or a suitable salts or derivatives thereof, Chromatography or HPLC. The compounds represented by general formula I may also be prepared by preparing from the corresponding optically pure intermediate or by removing the corresponding racemate with a suitable chiral carrier, for example with HPLC or fractional crystallization of the corresponding racemic and the diastereomeric salt formed by the reaction of a suitable acid or base having optical activity.

The compounds represented by general formula I may be in the form of tautomers, and the invention comprises a single tautomer and mixtures tautomers.

The present invention also comprises radiolabeled derivatives of compounds represented by general formula I, which are suitable for biological studies.

The present invention includes any prodrug form of the compound represented by general formula I.

The present invention also comprises pharmaceutically acceptable oxides of the compounds represented by general formula I, or pharmaceutically acceptable solvates thereof, including but not limited to hydrates.

The present invention also comprises a plurality of crystal forms of compounds represented by general formula I and various forms of various salts of the compounds represented by general formula I.

Another object of present invention is to provide a method for preparing the compounds represented by general formula I, which comprises:

(1) When Z is NH, 1) the compound I-2 is prepared by sulfonylation between bromide II and aminosulfonamide (compound VI) in which N atom is protected, deprotection, and amination reaction:

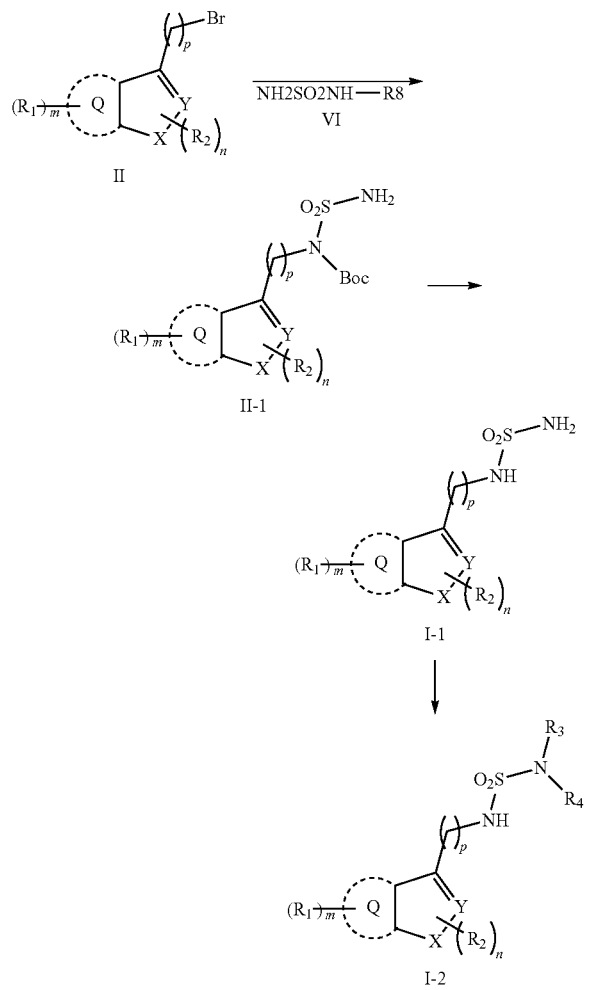

Wherein compound II and compound VI are subjected to sulfonylation in the presence of a base to give compound II-1, wherein R8 is a protecting group.

The deprotection method may be selected according to the nature of the protecting group, for example, R8 may be Boc, Cbz protecting group, and when R8 is Boc protecting group, the protecting group may be removed under acidic conditions such as hydrochloric acid, sulfuric acid or trifluoromethyl acetic acid.

The amination reaction can be carried out by the amination reaction of $R_3$-A, $R_4$-A or A-$R_3$-$R_4$—B with compound I-1 in the presence of a base, wherein A and B are the same or different, and are each independently Cl, Br or I;

Wherein the starting material bromides II are commercially available, or prepared by a known synthetic method known in the art or a method reported in the literature, for example, by the following method:

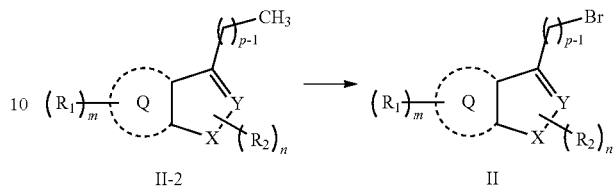

Compound II is prepared by brominating compound II-2 with brominating reagents which may be N-bromosuccinimide (NBS), $Br_2$, etc., and benzoyl peroxide or azobisisobutyronitrile and the like as catalysts can be further added thereto, as needed;

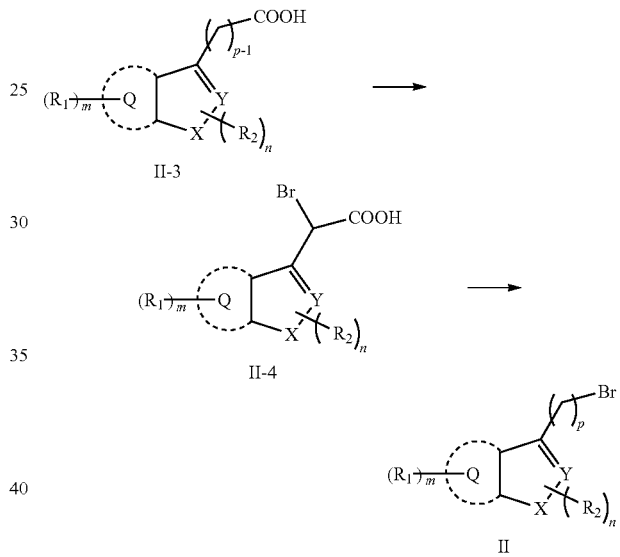

Compound II may also be prepared from compound II-3 via bromination and decarboxylation.

Wherein, the brominating reagent used in the bromination may be NBS, liquid bromine ($Br_2$) etc, and benzoyl peroxide or AIBN (azobisisobutyronitrile) and the like as catalysts can be further added thereto, as needed.

The decarboxylation reaction of compound II-4 can be carried out under heating conditions or other decarboxylation conditions; or 2) the compound I-2 is prepared by sulfonylation between bromides III and aminosulfonyl chloride (compound VII) in which N atom is protected, deprotection, and amination reaction:

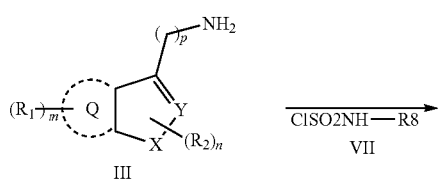

-continued

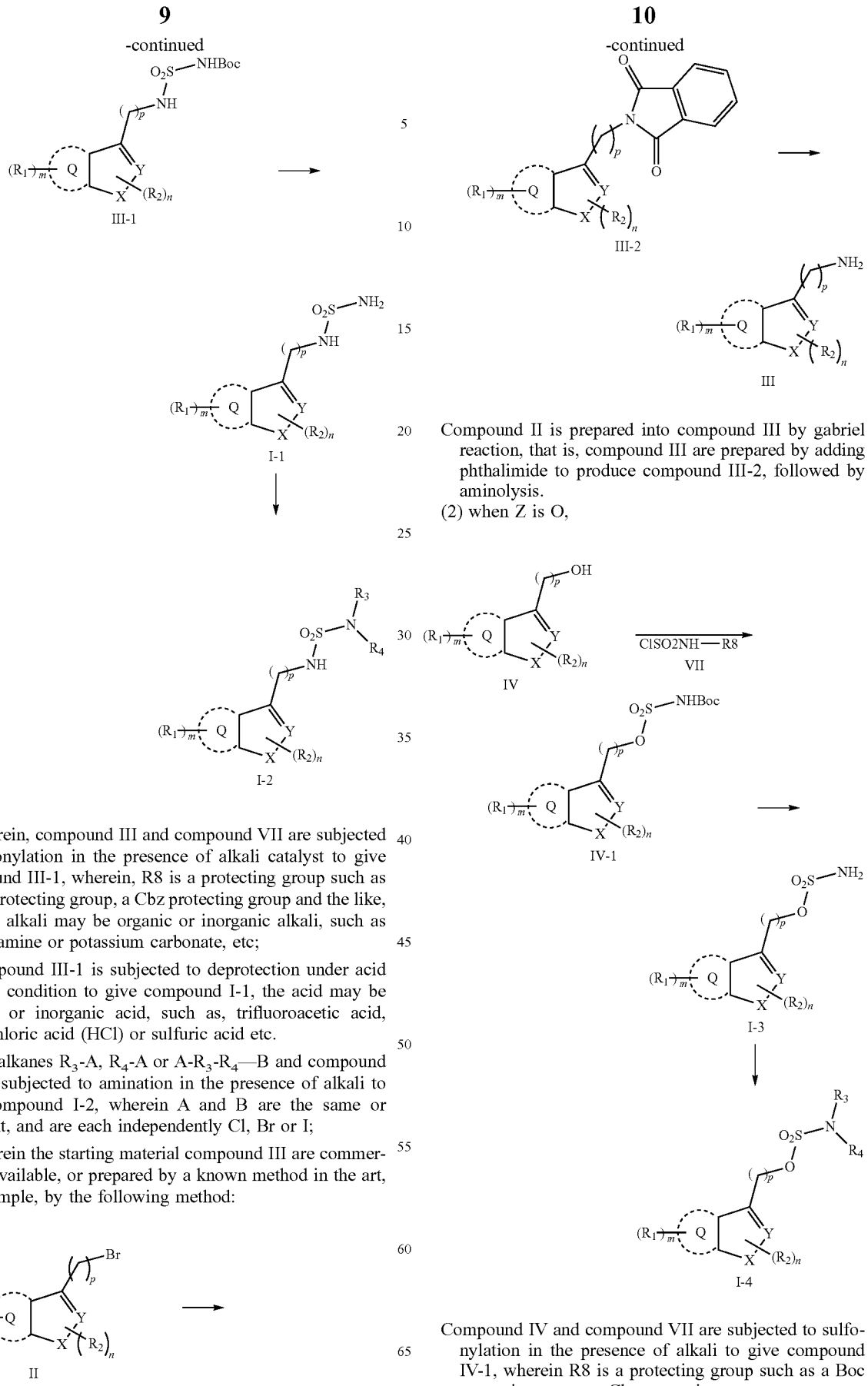

Compound II is prepared into compound III by gabriel reaction, that is, compound III are prepared by adding phthalimide to produce compound III-2, followed by aminolysis.

(2) when Z is O,

Wherein, compound III and compound VII are subjected to sulfonylation in the presence of alkali catalyst to give compound III-1, wherein, R8 is a protecting group such as a Boc protecting group, a Cbz protecting group and the like, and the alkali may be organic or inorganic alkali, such as triethylamine or potassium carbonate, etc;

Compound III-1 is subjected to deprotection under acid catalyst condition to give compound I-1, the acid may be organic or inorganic acid, such as, trifluoroacetic acid, hydrochloric acid (HCl) or sulfuric acid etc.

Haloalkanes $R_3$-A, $R_4$-A or A-$R_3$-$R_4$—B and compound I-1 are subjected to amination in the presence of alkali to give compound I-2, wherein A and B are the same or different, and are each independently Cl, Br or I;

Wherein the starting material compound III are commercially available, or prepared by a known method in the art, for example, by the following method:

Compound IV and compound VII are subjected to sulfonylation in the presence of alkali to give compound IV-1, wherein R8 is a protecting group such as a Boc protecting group, a Cbz protecting group, etc.

Or

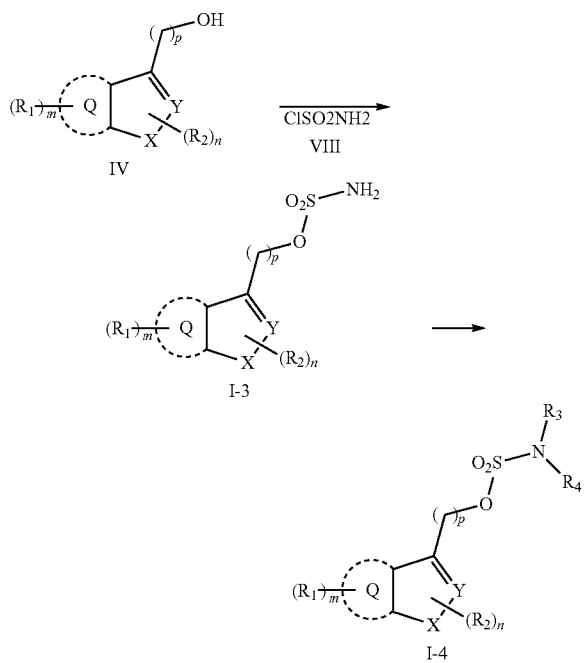

Compound IV and aminosulfonyl chloride (compound VIII) are reacted in the presence of alkali to directly give compound I-3, wherein the reaction condition are similar to that of corresponding reaction in method (1), or the reaction can be directly carried out without adding catalyst.

Compound I-3 is subjected to amination in the presence of alkali to give compound I-4;

Wherein the starting material hydroxyl compound (IV) may be commercially available, or prepared by a known method in the art;

(3) When Z is $CH_2$,

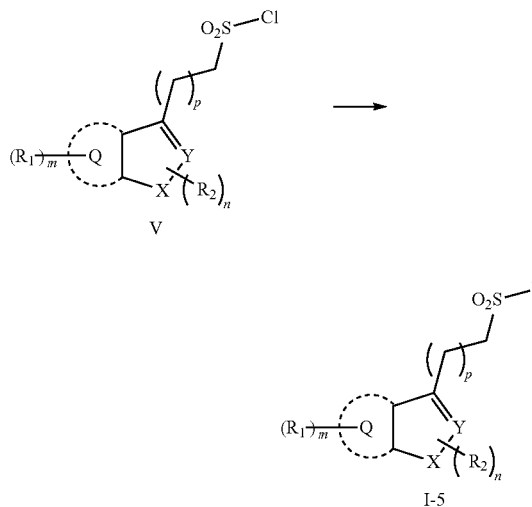

Compound V and corresponding amine $HNR_3R_4$ are subjected to amination to give compound I-5;

Wherein the compound V may be commercially available, or prepared by a known method in the art;

(4) When Z is $N-R_5$ or $CH-R_5$, the compound represented by general formula I can be prepared from the compound represented by general formula I-2 or general formula I-5 by alkylation reaction.

In the general formulas mentioned in the methods, X, Y, Q rings, m, n, p, $R_1$ and $R_2$ are defined same as in general formula I; $R_3$ and $R_4$ are defined same as above except that they are not H; $R_5$ is C1-C10 alkyl.

The above compound I, I-1, I-2, I-3, I-4 and I-5 are the target compound of the present invention.

According to still another aspect of the present invention, the present invention provides a pharmaceutical use of the aminosulfonyl-based compounds represented by the general formula I or tautomers, enantiomers, racemates or pharmaceutically acceptable salts thereof, a use as antiepileptics, anti-obesity agents, and a use in preparing medicine for treating diseases of convulsions, epilepsy (including partial epilepsy, generalized epilepsy, epileptic seizure as a complication of other diseases), obesity, etc.

According to still another aspect of the present invention, the present invention also provides a pharmaceutical composition comprising a therapeutically effective amount of aminosulfonyl-based compounds selected from the compounds represented by general formula I or tautomers thereof, enantiomers, racemates or pharmaceutically acceptable salts, which may be used as antiepileptics, anticonvulsants, anti-obesity agents, and the compositions may optionally comprise pharmaceutically acceptable carriers or excipients.

The composition is consisted of therapeutically effective amount of one or more aminosulfonyl-based compounds represented by general formula I (or pharmaceutically acceptable salts thereof, or pharmaceutically acceptable solvates thereof) and at least one pharmaceutically acceptable excipient. The selection for pharmaceutical excipients varies depending on route of administration and the characteristics and function of the excipients. Generally, the excipients are fillers, diluents, binders, wetting agents, disintegrants, lubricants, emulsifiers, suspending agents etc. The proportion of the compounds represented by general formula I of the present invention, the pharmaceutically acceptable salts thereof or the solvates thereof, in the above composition is 0.1% to 99.9% by weight, preferably 1% to 99% by weight, based on the total weight.

The pharmaceutically acceptable excipients refer to conventional drug carriers in the field of pharmacy, such as diluents, such as water, etc; fillers, such as starch, sucrose, etc; binders, such as cellulose derivatives, alginates, gelatins, polyvinyl pyrrolidone; wetting agents, such as glycerol; disintegrating agents, such as agar, calcium carbonate and sodium bicarbonate; absorption enhancers, such as quaternary ammonium compounds; surfactants, such as cetyl alcohol; adsorbent carriers, such as kaolin and hectorite clay; lubricants, such as talc, calcium stearates and magnesium stearates, and polyethylene glycols. In addition, other adjuvants such as flavoring agents and sweetening agents may also be added to the pharmaceutical composition.

The present invention also provides a method for preparing a pharmaceutically acceptable composition comprising an aminosulfonyl-based compound represented by the general formula I, a pharmaceutically acceptable salt thereof or a solvate thereof. The aminosulfonyl-based compound represented by the general formula I, its pharmaceutically acceptable salt or its solvate is usually mixed with a pharmaceutically acceptable excipient and formulated in a conventional manner to a form suitable for a certain route of administration (dosage form). Dosage forms include tablets, capsules, granules, pills, solutions, suspensions, emulsions, ointments, liners, creams, aerosols, injections, suppositories, etc. Preferably, the dosage forms include tables and capsules.

The compounds of the present invention are generally used in a dose of 1 to 500 mg, preferably 10 to 100 mg, per day, in multiple or multiple administration. If necessary, the dose can be suitably deviate from the above range. The optimal dose can be determined by professional based on specific circumstances and professional knowledge. The circumstances include the severity of the disease, individual differences in the patients, the characteristics of the formulation, and the route of administration, et al.

In addition, the present invention also provides a use of the pharmaceutically acceptable composition comprising an aminosulfonyl-based compounds represented by the general formula I, pharmaceutically acceptable salts thereof or solvates thereof as medicine for human.

According to still another aspect of the present invention, the present invention also provides a method for treating seizures, epilepsy comprising partial epilepsy, generalized epilepsy, epileptic seizures as complications of other diseases, and obesity, and the method comprises administering therapeutically effective amount of one or more of aminosulfonyl-based compounds represented by general formula I, tautomers, enantiomers, racemates or a pharmaceutically acceptable salts thereof, or the pharmaceutical composition of the present invention.

The compounds or compositions provided by the present invention may be administrated by oral route, injection (intravenous injection, intramuscular injection, subcutaneous injection and intracoronary injection), sublingual route, buccal route, transrectal route, transurethral route, transvaginal route, nasal route, inhalation or local delivery. The oral route is preferred. For oral administration, the compounds may be formulated into conventional solid preparations such as tablets, powders, granules, capsules, etc., or made into liquid preparations such as water or oil suspensions, or other liquid preparations such as syrup. In the case of parenteral administration, the compounds can be used as a solution for injection, water or oil suspensions.

The present invention also provides a use of the pharmaceutically acceptable composition comprising aminosulfonyl-based compounds represented by the general formula I, pharmaceutically acceptable salts thereof or solvates thereof in preparing the human medicine for treating epilepsy or related diseases.

The aminosulfonyl-based compounds represented by the general formula I exhibit significant antiepileptic efficacy in animal models, and are effective in treating epilepsy, convulsions or epilepsy-related diseases, in particular they can reduce the mortality of epileptic seizures, have good protective effect and less side effect.

The compounds represented by general formula I of the present invention also have effect in reducing weight, which can reduce body weight of obese rats and reduce total cholesterol and triglyceride levels.

Sulfonamide antiepileptic drugs such as thiazide, topiramate and zonisamide have significant inhibitory effect on carbonic anhydrase in kidney. Long-term administration of such drugs may easily lead to metabolic acidosis, kidney stones, osteoporosis which increases risk of fracture, stunted growth of child, affecting the development of fetal (FDA label of topiramate and zonisamide), which limits the population for taking medicine and lowers the safety for taking medicine. Comparing with the available sulfonamide drugs, the compounds provided by present invention have a significant lowered inhibitory effect on carbonic anhydrase, and they are anticipated to have a better clinical safety for using drugs and be suitable for larger population.

Thus, the compounds provided by the present invention are expected to exhibit better clinical safety and efficacy.

DETAILED DESCRIPTION OF EXEMPLARY EMBODIMENTS

The following examples further illustrate the synthesis of the compounds of the present invention and their intermediates, but are not intended to limit the scope of the invention. $^1$H NMR is conducted on nuclear magnetic resonance spectrometer, Mercury-400 or Mercury-300 (Varian). The abbreviations are as follows: s, singlet; d, doublet; t, triplet; q, quartet; m, multiplet; br, broad. The starting materials are prepared according to literature or purchased from the market.

Example 1: N-[(6-chloro-benzo[d]isoxazol-3-yl)methyl]-sulfamide

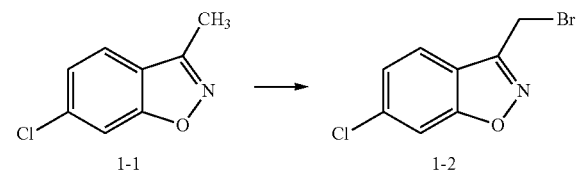

Compound 6-chloro-3-methylbenzisoxazole (compound 1-1) (300 mg, 1.8 mmol) was added into dry carbon tetrachloride (10 ml), and NBS (N-bromosuccinimide (410 mg, 1.8 mmol), and then benzoyl peroxide (44 mg, 0.18 mmol) were added thereto. After completion of the addition, the reaction was conducted by heating the resultant mixture to reflux for 12 hours under nitrogen atmosphere. After cooling to room temperature, the reaction fluid was filtered, and the filtrate was condensed to dryness. The resultant was subjected to column chromatography to give yellowish solid compound 1-2 (150 mg).

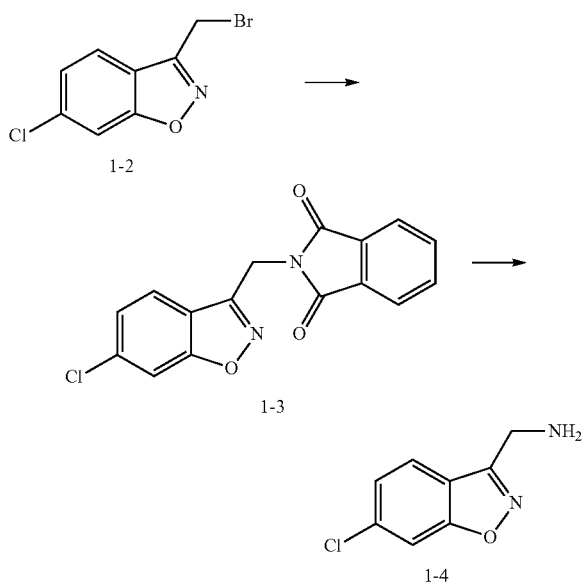

Compound 1-2 (150 mg, 0.61 mmol) was added to acetonitrile (10 ml), and phthalimide (130 mg, 0.61 mol) was added thereto. After heating to reflux for 2 hours, the reaction was monitored by TLC until the reaction was completed. The reaction liquid was directly concentrated to dryness, then dichloromethane was added thereto. The resultant was washed with water and saturated brine, dried over anhydrous sodium sulfate. The sodium sulfate was filtered off and the filtrate was concentrated to give the product 1-3 (200 mg) as a light red solid, which can be used directly to the next reaction.

Compound 1-3 (200 mg, 0.63 mmol) was added to methanol (10 ml), and then hydrazine hydrate (70 mg, 1.3 mmol) was added thereto. After heating to reflux for 1 hour, the reaction was monitored by TLC until the reaction was completed. The reaction liquid was directly concentrated to dryness to give the oily product (crude product), which was further diluted with dichloromethane, washed with water and saturated brine, dried over anhydrous sodium sulfate, and filtered. The filtrate was concentrated, and separated by column chromatography to give compound 1-4 as white solid product (80 mg).

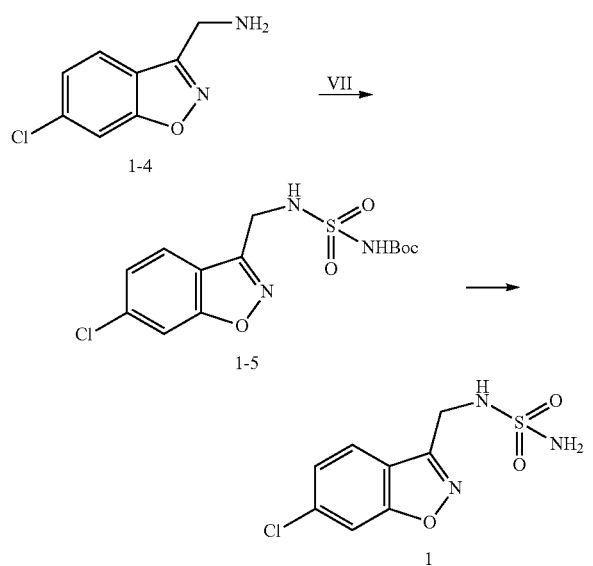

Tert-butanol (300 mg, 4 mmol) and dichloromethane (10 ml) were mixed and the chlorosulfonyl isocyanate (560 mg, 4 mmol) was slowly added dropwise under cooling condition of ice-water bath. After the addition was finished, the reaction was continued for half an hour to give product N-Boc-chlorosulfonamide solution which can be used directly in the next step.

The compound 1-4 (80 mg, 0.44 mmol) was added to dichloromethane (10 ml), triethylamine (90 mg, 0.9 mmol) was added thereto, and the obtained N-Boc-chlorosulfonamide was slowly added dropwise under cooling condition of ice-water bath until the starting material compound 1-4 was run out. The reaction liquid was washed with water once, diluted hydrochloric acid once, saturated brine once, dried over anhydrous sodium sulfate, and filtered. The filtrate was concentrated, and separated by column chromatography to give compound 1-5 as white solid (100 mg).

Compound 1-5 (100 mg, 0.28 mmol) was added to dichloromethane (10 ml), and then trifluoroacetic acid (1 ml) was added thereto, and mixture was heated to 40° C. to react for 1 hour. The reaction was monitored by TLC until the reaction was completed. The reaction liquid was directly concentrated to dryness, and resultant was further diluted with dichloromethane, washed with water and saturated brine once, dried over anhydrous sodium sulfate, and filtered. The filtrate was concentrated, and separated by column chromatography to give compound 1 as white solid product (10 mg).

$^1$H NMR (DMSO-$d_6$) δ: 7.95 (d, 1H), 7.76 (d, 1H), 7.41 (t, 1H), 7.30 (s, 1H), 6.77 (s, 2H), 4.39 (d, 2H);

EI-MS m/z: 261 (M), 263 (M+2).

Example 2: N-[(6-fluoro-benzo[d]isoxazol-3-yl)methyl]-sulfamide

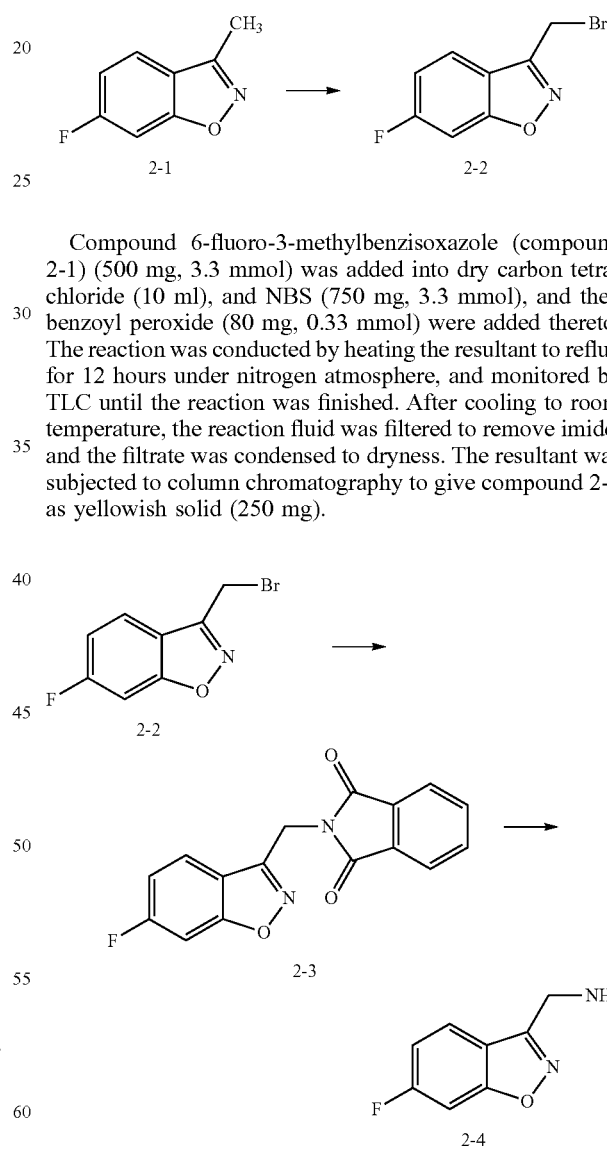

Compound 6-fluoro-3-methylbenzisoxazole (compound 2-1) (500 mg, 3.3 mmol) was added into dry carbon tetrachloride (10 ml), and NBS (750 mg, 3.3 mmol), and then benzoyl peroxide (80 mg, 0.33 mmol) were added thereto. The reaction was conducted by heating the resultant to reflux for 12 hours under nitrogen atmosphere, and monitored by TLC until the reaction was finished. After cooling to room temperature, the reaction fluid was filtered to remove imide, and the filtrate was condensed to dryness. The resultant was subjected to column chromatography to give compound 2-2 as yellowish solid (250 mg).

Except that compound 2-2 (250 mg, 1.09 mmol) was used as a starting material, compound 2-4 (120 mg) was prepared in the same manner of preparing the compound I-4 from compound 1-2 in Example 1.

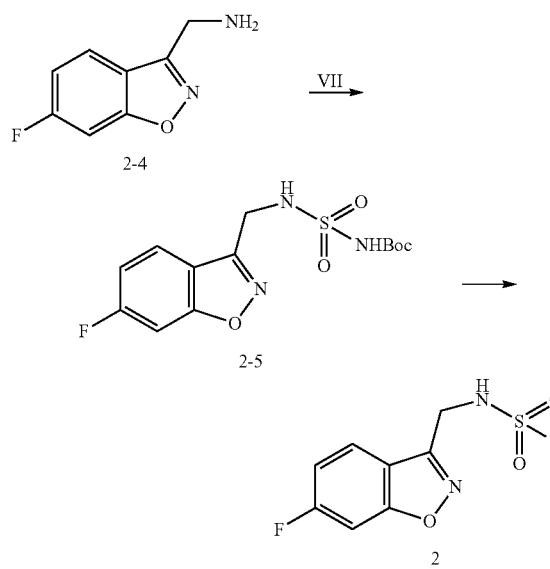

Except that compound 2-4 (120 mg, 0.72 mmol) was used as a starting material, compound 2 (80 mg) was prepared in the same manner of preparing the compound 1 from compound 1-4 in EXAMPLE 1.

$^1$H NMR (DMSO-$d_6$) δ: 7.75 (d, 1H), 7.41 (t, 1H), 7.26 (d, 1H), 6.91 (s, 1H), 6.77 (s, 2H), 4.36 (d, 2H);

EI-MS m/z: 245 (M), 165 (base peak), 137.

Example 3: N-[(benzo[d]isoxazol-3-yl)methyl]-sulfamide

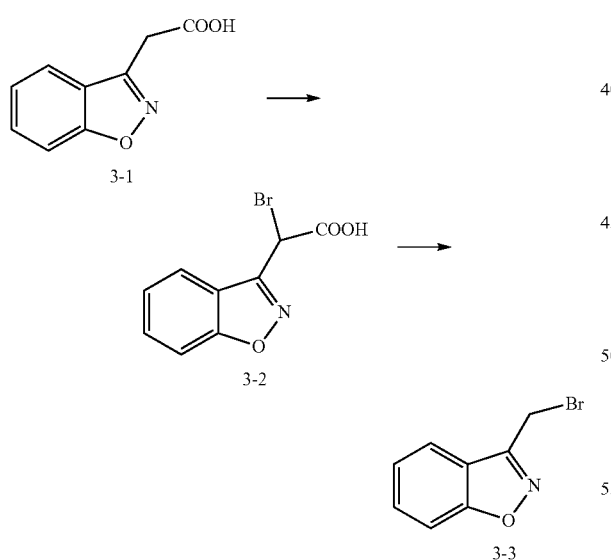

1,2-benzisoxazole-3-acetic acid (compound 3-1) (5 g, 0.028 mol) was added to the reaction flask, acetic acid (20 ml) was added, and then liquid bromide (4.5 g, 0.028 mol) were added thereto dropwise at room temperature. After completion of the addition, the mixture was further heated to 40° C. for 2 hours, and was monitored by TLC until the reaction was completed. The reaction liquid was poured into ice water, and the solid product was precipitated. After stirring for half an hour, the resultant was filtered and dried to obtain a pale yellow solid product (compound 3-2, 6 g).

The pale yellow solid product (compound 3-2, 6 g, 0.024 mol) obtained above was added to the reaction flask and then toluene (60 ml) was added thereto. After heating to reflux for 12 hours, and the reaction was monitored by TLC until the reaction was completed. The reaction liquid was concentrated to dryness to give the product as a pale red solid 3-bromomethyl-1,2-benzisoxazole (compound 3-3, compound of general formula II) (4.5 g) which was used directly in the next step without purification.

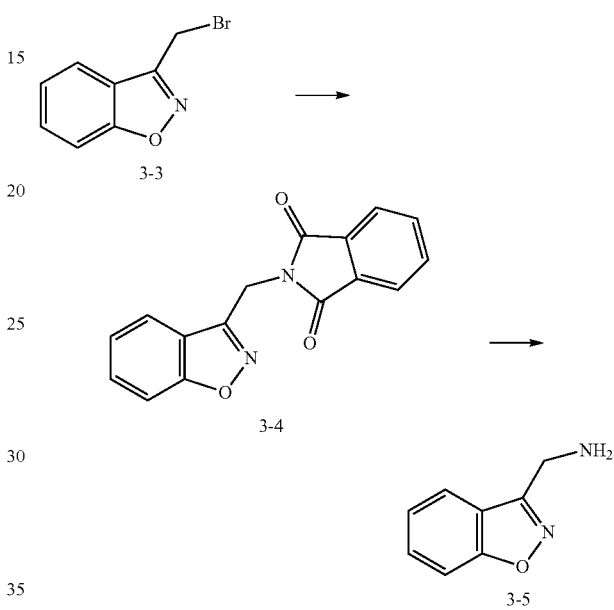

Except that 3-bromomethyl-1,2-benzisoxazole (compound 3-3) (4.5 g, 0.021 mol) was used as a starting material, compound 3-5 (3 g) as white solid product was prepared in the same manner of preparing the compound 1-4 from compound 1-2 in EXAMPLE 1.

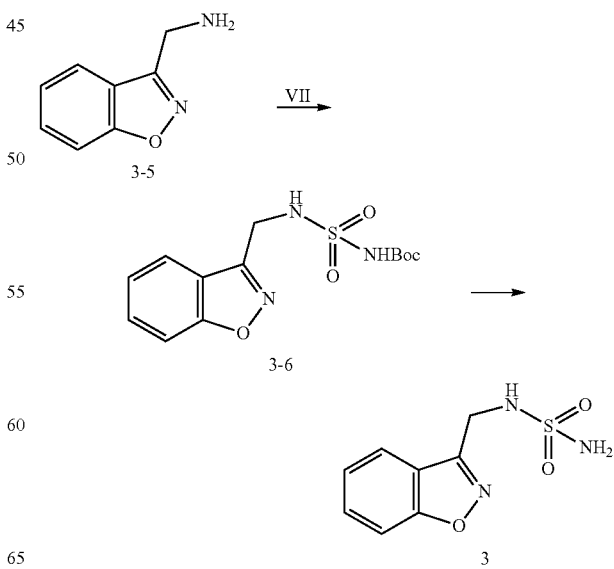

Except that 3-aminomethyl-1,2-benzisoxazole (compound 3-5) (3 g, 0.02 mol) was used as a starting material, compound 3 (1.3 g) as white solid product was prepared in the same manner of preparing the compound 1 from compound 1-4 in EXAMPLE 1.

$^1$H NMR (DMSO-d$_6$) δ: 8.03 (dt, 1H), 7.74 (d, 1H), 7.66 (td, 1H), 7.47-7.38 (m, 2H), 6.86 (s, 2H), 4.47 (d, 2H);

EI-MS m/z: 227 (M).

Example 4: N-[(6-fluoro-benzopyrazol-3-yl)methyl]-sulfamide

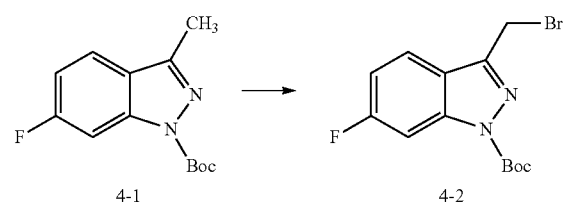 [SMILES: Cc1nn(C(=O)OC(C)(C)C)c2cc(F)ccc12 ; CC(C)(C)OC(=O)n1nc(CBr)c2ccc(F)cc21]

6-fluoro-N-Boc-3-methylbenzopyrazole (compound 4-1) (500 mg, 2.15 mmol) and dry carbon tetrachloride (10 ml) were added to the reaction flask, NBS (490 mg, 2.15 mmol) and benzoyl peroxide (55 mg, 0.22 mmol) were added thereto, and the mixture was heated to reflux for 12 hours under nitrogen atmosphere. After completion of the reaction, the reaction liquid was cooled to room temperature and then filtered. The filtrate was concentrated and separated by column chromatography to give the compound 4-2 as a pale yellow solid (250 mg).

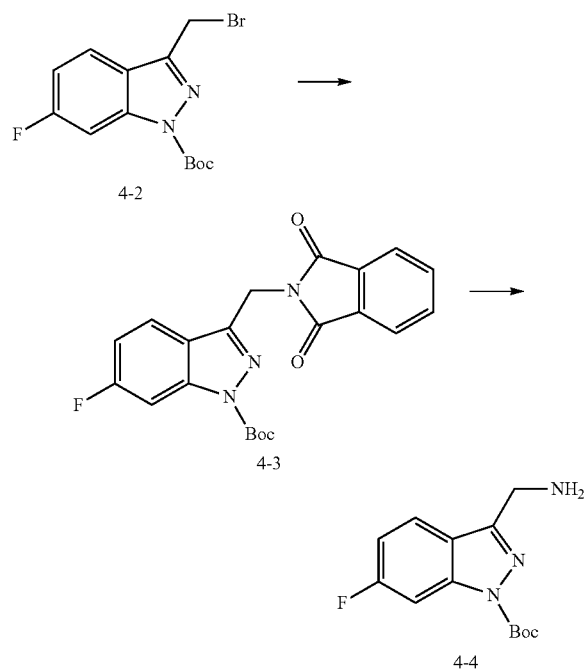

Compound 4-2 (250 mg, 0.8 mmol), acetonitrile (10 ml) was added to reaction flask, and phthalimide (170 mg, 0.8 mol) was added thereto. After heating to reflux for 2 hours, the reaction was monitored by TLC until the reaction was completed. The reaction liquid was directly concentrated to dryness, then dichloromethane was added thereto. The resultant was washed with water and saturated brine once, dried over anhydrous sodium sulfate, filtered, and concentrated to give the compound 4-3 (250 mg) as a light red solid, which can be used directly to the next reaction without purification.

Compound 4-2 (250 mg, 0.7 mmol), methanol (10 ml) was added to reaction flask, and then hydrazine hydrate (70 mg, 1.4 mmol) was added thereto. After heating to reflux for 1 hour, the reaction was monitored by TLC until the reaction was completed. The reaction liquid was directly concentrated to dryness to give the oily product (crude product) which was further diluted with dichloromethane, washed with water and saturated brine once, dried over anhydrous sodium sulfate, and filtered. The filtrate was concentrated, and separated by column chromatography to give compound 4-4 as white solid product (120 mg).

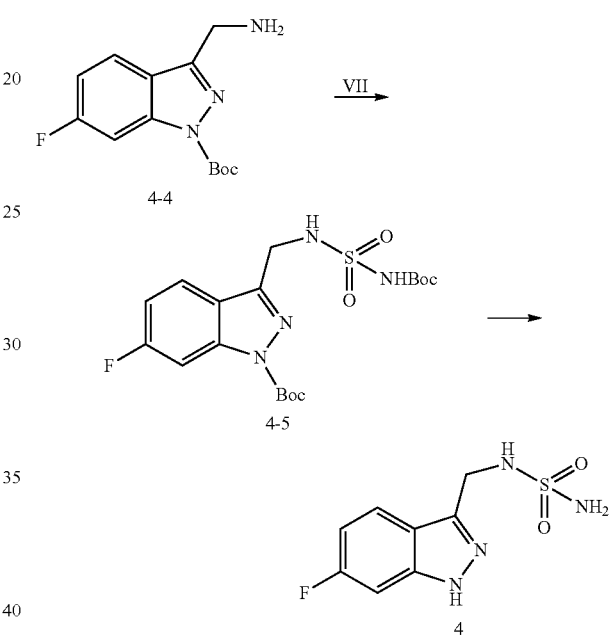

The compound 4-4 (120 mg, 0.48 mmol), dichloromethane (10 ml) were added to reaction flask, and triethylamine (100 mg, 1 mmol) was added thereto. A solution of N-Boc-chlorosulfonamide (compound VII, prepared according to EXAMPLE 2) was slowly added dropwise under cooling condition of ice-water bath until the starting material was run out. The reaction liquid was washed with water once, diluted hydrochloric acid once, saturated brine once, dried over anhydrous sodium sulfate, and filtered. The filtrate was concentrated, and separated by column chromatography to give compound 4-5 as white solid (160 mg).

Compound 4-5 (160 mg, 0.38 mmol), dichloromethane (10 ml), and then trifluoroacetic acid (1 ml) were added to a reaction flask. The mixture was heated to 40° C. to react for 1 hour. The reaction was monitored by TLC until the reaction was completed. The reaction liquid was directly concentrated to dryness, and resultant was further diluted with dichloromethane, washed with water and saturated brine once, dried over anhydrous sodium sulfate, and filtered. The filtrate was concentrated, and separated by column chromatography to give compound 4 as white solid product (40 mg).

$^1$H NMR (DMSO-d$_6$) δ: 12.81 (s, 1H), 7.90 (d, 1H), 7.49 (d, 1H), 7.35 (t, 1H), 7.02 (t, 1H), 6.69 (s, 2H), 4.40 (d, 2H);

EI-MS m/z: 244.

Example 5: N-[(5-nitro-benzo[d]isoxazol-3-yl)methyl]-sulfamide

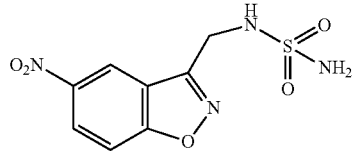

The target compound was prepared by using 5-nitro-3-methyl-benzisoxazole as starting material with reference to the method in EXAMPLE 1.

EI-MS m/z: 244.

Example 6: N-[(5-methoxy-benzo[d]isoxazol-3-yl)methyl]-sulfamide

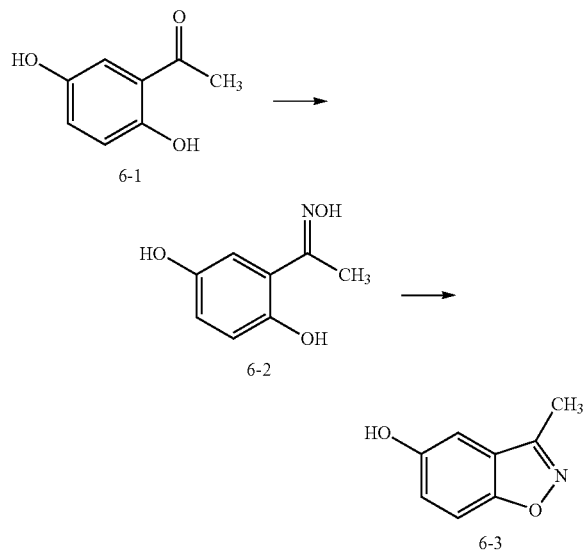

2,5-dihydroxyacetophenone (compound 6-1) (4.5 g, 30 mmol) was dissolved in pyridine (17 ml), $NH_2OH \cdot H_2O$ (2.1 g, 30 mmol) was added in batches and stirred overnight at room temperature. After the completion of the reaction was confirmed by TLC, the mixture was extracted with ethyl acetate. The organic layer was washed successively with water, 0.2 M HCl solution, concentrated to dryness under reduced pressure. Toluene was added thereto, and the resultant was concentrated under reduced pressure and dried to give solid compound 6-2 (4.63 g).

PPh$_3$ (triphenylphosphine) (3.14 g, 13 mmol) was dissolved in dry dichloromethane (50 ml), and DDQ (2,3-dichloro-5,6-dicyano-p-benzoquinone) (2.72 g, 12 mmol) was added thereto. The above obtained compound 6-2 was slowly added thereto under stirring. After the completion of the reaction was confirmed by TLC, the resultant was concentrated to remove solvent, and the residue was separated by column chromatography to give compound 6-3.

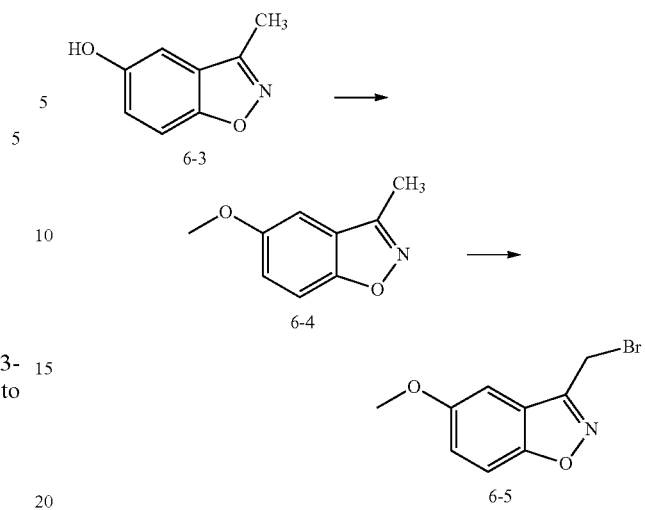

Compound 6-3 (727 mg, 4.8 mmol) was dissolved in acetonitrile, potassium carbonate (1.35 g, 9.6 mmol) and dimethyl sulfate (43 µl, 7.2 mmol) were added thereto and the mixture was heated at 50° C. After the completion of the reaction was confirmed by TLC, the resultant was concentrated to remove solvent, extracted with ethyl acetate and water. The ethyl acetate layer was washed with saturated brine, dried, concentrated and separated by column chromatography to give compound 6-4.

Compound 6-4 (390 mg, 2.4 mmol) was dissolved in CCl$_4$, NBS was added, and then AIBN (azobisisobutyronitrile) was added thereto. The mixture was heated at 60° C. for half an hour and then raised to 80° C. After the completion of the reaction was confirmed by TLC, the reaction liquid was cooled, diluted with dichloromethane, and then water was added thereto to perform extraction. The organic layer was washed with saturated brine, dried and concentrated to give compound 6-5, which can be used directly in next step without purification.

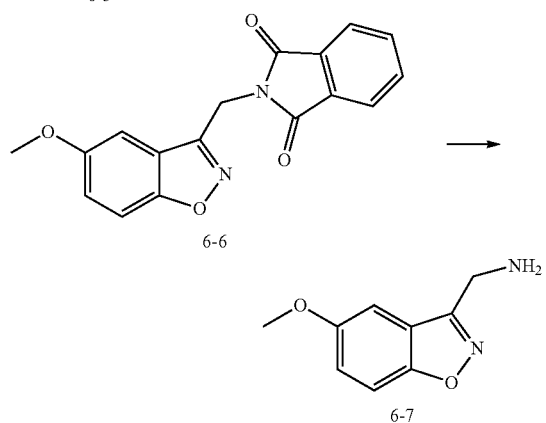

The product 6-5 (200 mg) obtained above was dissolved in DMF, potassium phthalimide was added and stirred at room temperature for 30 min. The solvent was evaporated to dryness to give compound 6-6, which was used directly in the next step.

The compound 6-6 obtained above was dissolved in methanol, the hydrazine hydrate was added, the mixture was heated to reflux. After the TLC confirmed that the reaction was completed, the reaction mixture was concentrated, and then dichloromethane was added thereto. The resultant was washed with water, saturated brine, dried, concentrated and separated by column chromatography to give compound 6-7.

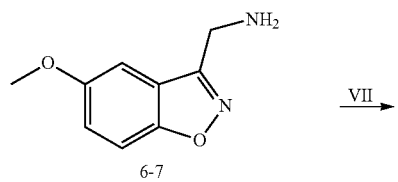

6-7

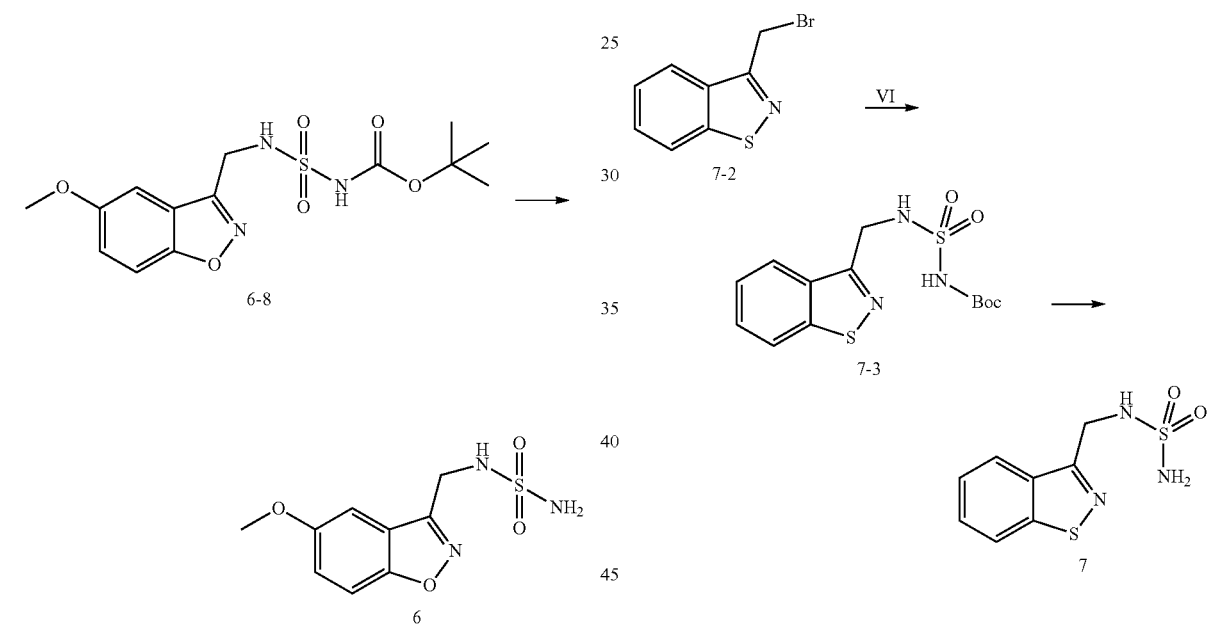

Compound 6-7 was dissolved in dichloromethane (4 ml), triethylamine (0.42 ml) was added, and a fresh solution of N-Boc-chlorosulfonamide (1 ml) (compound VII, prepared with reference to Example 2) was slowly added in ice bath. After the reaction was completed, the reaction solution was washed with water, diluted hydrochloric acid and saturated brine, and the organic layer was dried and concentrated to give product 6-8 (53 mg).

Compound 6-8 was dissolved in dichloromethane (2 ml), trifluoroacetic acid (0.3 ml) was added thereto and the mixture was reacted at room temperature for 1 h. After the reaction is completed, the reaction mixture was concentrated, a small amount of dichloromethane was added thereto, stirred and filtered to give pure compound 6 (24 mg).

$^1$H NMR(CD$_3$OD-d$_4$) δ: 7.45 (dd, 1H), 7.38 (d, 1H), 7.17 (dd, 1H), 4.52 (s, 2H), 3.82 (s 3H).

Example 7: N-[(benzo[d]isothiazol-3-yl)methyl]-sulfamide

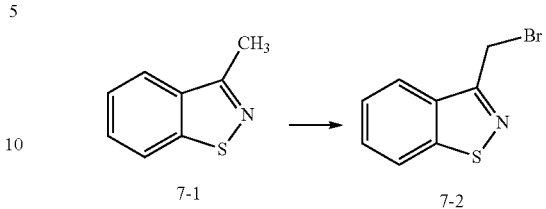

Compound 7-1 (870 mg) and AIBN (10 mg) were added to CCl$_4$, NBS (1.14 g) and AIBN (10 mg) were added and the mixture was heated at reflux. After 3 hours, stop heating, the mixture was cooled and diluted with CH$_2$Cl$_2$. The organic layer was dried over anhydrous sodium sulfate, filtered to remove sodium sulfate and concentrated to give compound 7-2 (1.3 g).

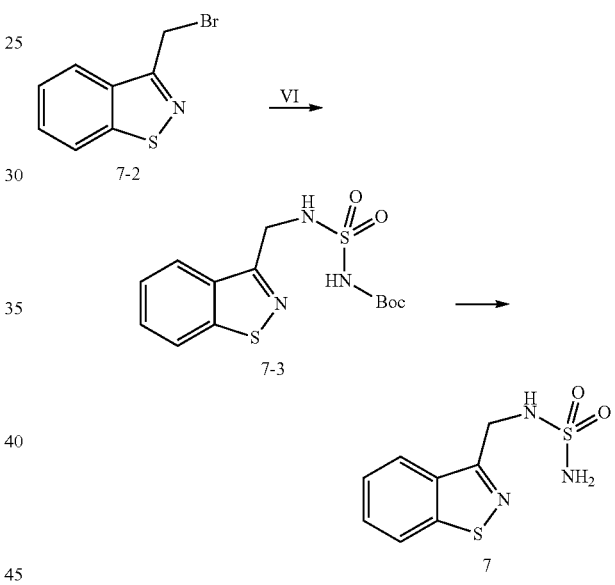

The compound VI (N-Boc-aminosulfonamide) (3.5 g, 8 eq) and K$_2$CO$_3$ were added to DMF. Compound 7-2 (500 mg) was added thereto and stirred at room temperature. After the reaction was completed, the resultant was concentrated under reduced pressure to dryness. Water and CH$_2$Cl$_2$ were added to extract the resultant, the obtained organic layer was washed, dried, concentrated to give compound 7-3 (2.3 g, crude).

The compound 7-3 (500 mg) obtained above was dissolved in CH$_2$Cl$_2$, and CF$_3$COOH was added thereto and stirred at room temperature. The reaction was complete after 4 hours. The resultant was concentrated to dryness, water and CH$_2$Cl$_2$ were added to extracted the resultant. The organic layer was washed, dried and concentrated. The target compound 7 of Example 7 (41 mg) was obtained by column chromatography.

$^1$H NMR (DMSO-d$_6$) δ: 8.30 (d, 1H), 8.19 (d, 1H), 7.62 (t, 1H), 7.52 (t, 1H), 7.23 (t, 1H), 6.76 (s, 2H), 4.52 (d, 2H);

EI-MS m/z: 243 (M$^+$), 163, 135, 91.

Example 8: N-[(benzo[d]isoxazol-3-yl)methyl]-N'-methyl-sulfamide

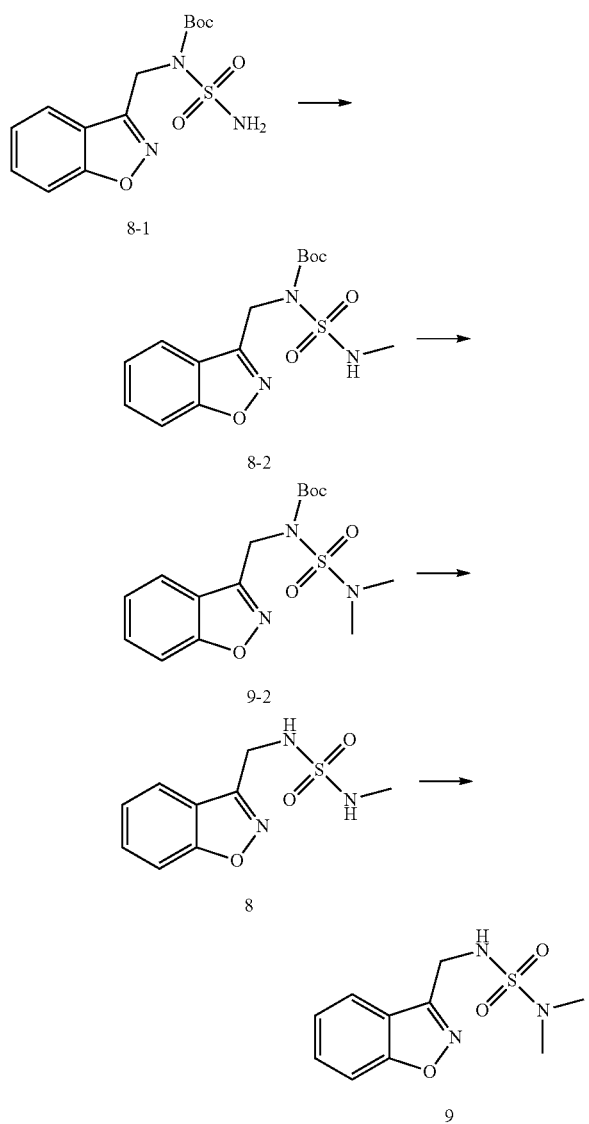

Compound 8-1 (400 mg), sodium hydride (88 mg) and DMF (3 ml) were added, and then methyl iodide (0.076 ml, 1 eq) was added thereto to react at room temperature under stirring. The reaction was stopped after 1 hour, ammonium chloride solution was added to the reaction liquid. The resultant was concentrated to remove DMF, dichloromethane and water were added to perform extraction. The organic phase was dried, concentrated to give compound 8-2 and 9-2 as yellow oil compound. Dichloromethane (2 ml), trifluoroacetic acid (2 ml) were added and the resultant was stirred at room temperature for 1 hour. The reaction was monitored by TLC until the reaction was completed. The solvent was removed by concentration, saturated sodium bicarbonate solution was added to adjust pH to weak alkaline. The resultant was extracted, concentrated, and separated by silica gel plates to give compound 8 (60 mg) and compound 9 (100 mg) as the final product.

Compound 8:
$^1$H NMR (DMSO-$d_6$) δ: 8.01 (d, 1H), 7.75 (t, 2H), 7.66 (t, 1H), 7.42 (t, 1H), 6.95 (q, 1H), 4.43 (d, 2H), 2.45 (d, 3H); EI-MS m/z: 242, 148, 123, 94.

Example 9: N-[(benzo[d]isoxazol-3-yl)methyl]-N',N'-dimethyl-sulfamide

The product obtained by using the same method as that in EXAMPLE 8 was separated by silica gel plates to give compound 9 as the final product.

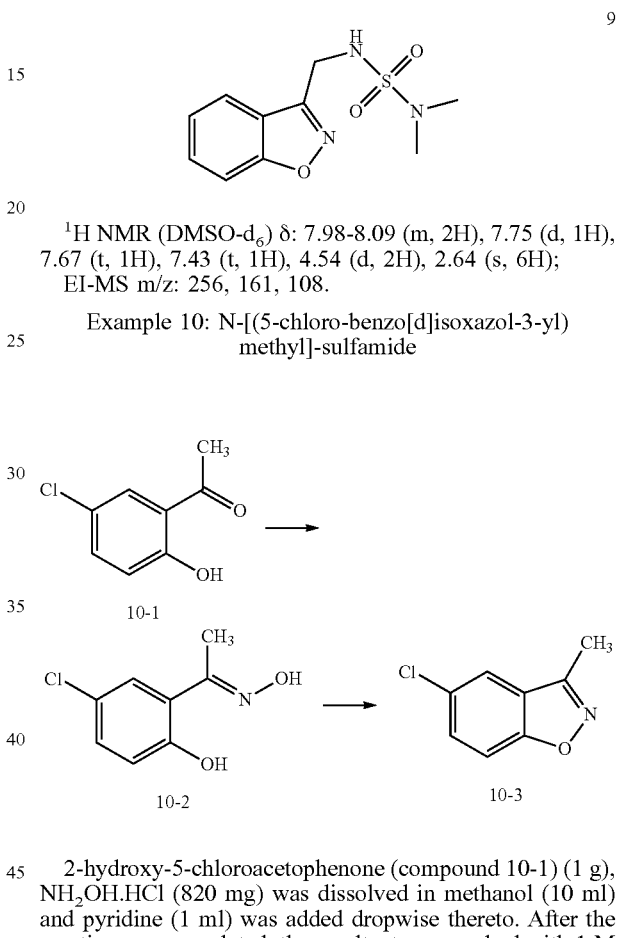

$^1$H NMR (DMSO-$d_6$) δ: 7.98-8.09 (m, 2H), 7.75 (d, 1H), 7.67 (t, 1H), 7.43 (t, 1H), 4.54 (d, 2H), 2.64 (s, 6H); EI-MS m/z: 256, 161, 108.

Example 10: N-[(5-chloro-benzo[d]isoxazol-3-yl)methyl]-sulfamide 2-hydroxy-5-chloroacetophenone (compound 10-1) (1 g), NH$_2$OH.HCl (820 mg) was dissolved in methanol (10 ml) and pyridine (1 ml) was added dropwise thereto. After the reaction was completed, the resultant was washed with 1 M HCl solution and water, extracted with water and ethyl acetate. The organic layer was washed, dried and concentrated to give compound 10-2 (1.07 g).

PPh$_3$ (2.12 g) was dissolved in dry CH$_2$Cl$_2$ (5 ml). DDQ (1.83 g) was added thereto under stirring, and then compound 10-2 (1 g) was added under stirring. After 20 minutes, the reaction was completed, the resultant was dried to evaporate solvent, and separated by column chromatograph to give compound 10-3 (450 mg).

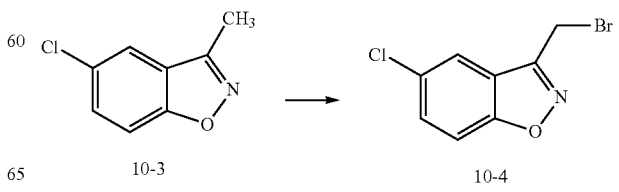

Compound 10-3 (383 mg) and AIBN (8 mg) were dissolved in CCl$_4$ and heated at 80° C. to reflux. NBS (490 mg) and AIBN (8 mg) were added thereto, and refluxed overnight. Then the resultant was diluted with CH$_2$Cl$_2$, and water was added thereto to separate layers. The organic layer was washed, and concentrated to give compound 10-4 (650 mg).

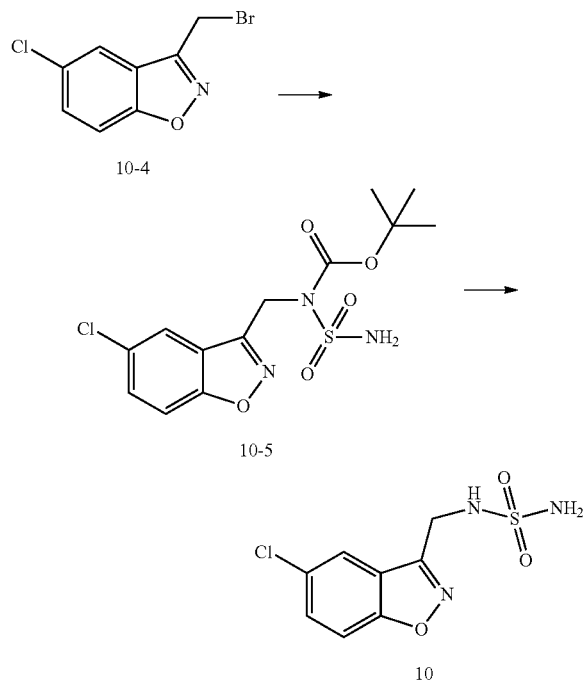

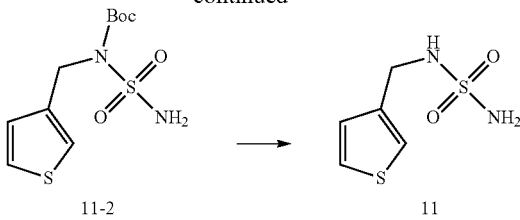

Compound VI (N-Boc-aminosulfonamide) (2.4 g) and K$_2$CO$_3$ (1.68 g) were added to DMF (20 ml) and the product 10-4 (600 mg) obtained in the previous step was added thereto. After the reaction was completed in 30 minutes, the resultant was concentrated to remove solvent under reduced pressure. Then, water was added and the mixture was extracted with CH$_2$Cl$_2$. The organic layer was washed, dried and concentrated to give compound 10-5 (650 mg).

Compound 10-5 (200 mg) was dissolved in CH$_2$Cl$_2$, CF$_3$COOH (0.4 ml) was added and stirred at room temperature. After the reaction was completed in 2 hours, the solvent was evaporated to dryness. The resultant was separated by column chromatograph to give compound 10 (40 mg).

$^1$H NMR (DMSO-d$_6$) δ: 10.57 (s, 1H), 10.02 (s, 1H), 8.07 (s, 1H), 7.03-7.15 (m, 2H), 6.92 (d, 1H), 4.25 (d, 2H);

EI-MS m/z: 261 (M), 263 (M+2).

Example 11: N-[(thiophen-3-yl)methyl]-sulfamide

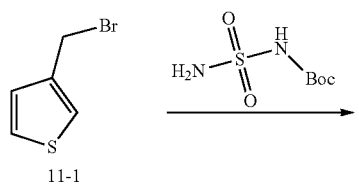

3-bromo methylthiophene (compound 11-1), 354 mg (2.0 mmol, 1.0 eq) were dissolved in DMF (5.0 ml), and N-Boc sulfonamide (432 mg, 2.2 mmol, 1.1 eq) (Compound VII, prepared with reference to Example 2) was added and then potassium carbonate (1.1 g, 8.0 mmol, 4.0 eq) was added thereto. And the reaction was stirred at room temperature overnight. The reaction liquid was poured into ice water (50 ml) and the viscous oil was precipitated. And ethyl acetate was added to extract twice. The organic phase was combined, washed with water twice, with brine once, dried over sodium sulfate, filtered and concentrated to dryness to give viscous oil. The crude obtained above was purified by chromatography (eluent, dichloromethane/Me(O)H=100/1 to 10/1), and the product was collected and concentrated to give compound 11-2 (320 mg, yield 56%).

The compound 11-2 (320 mg) obtained in the previous step was dissolved in anhydrous methanol (3.0 ml), and cooled to 0° C. in an ice bath. And then, hydrogen chloride in ethanol (3.0 ml) was added, and the mixture was warmed to room temperature and stirred at room temperature overnight. The reaction liquid was concentrated to dryness and the residue was purified by column chromatography (eluent DCM/Me(O)H=100/1 to 10/1). The product was collected, concentrated, and the residue was slurried in dichloromethane (3.0 ml). And the resultant was filtered and dried to give pure compound 11 (88 mg) as a white solid with yield of 42%.

$^1$H NMR (DMSO-d$_6$) δ: 7.48 (dd, 1H), 7.34 (m, 1H), 7.10 (dd, 1H), 6.99 (t, 1H), 6.60 (s, 2H), 4.06 (d, 2H);

ESI-MS m/z: 191.01 (M−1).

Example 12: N-[(thieno[3,2-b]thiophen-3-yl)methyl]-sulfamide

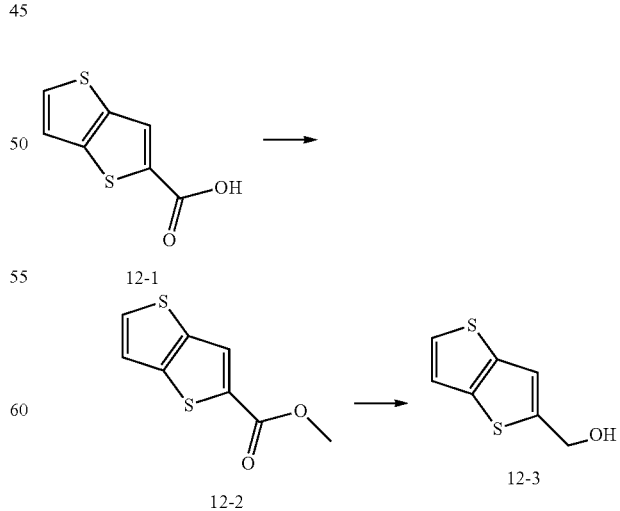

thieno[3,2-b]thiophen-2-formic acid (compound 12-1) 500 mg (2.7 mmol, 1.0 eq) was added to methanol (5.0 ml).

The mixture was cooled to 0° C., and then concentrated sulfuric acid (265 mg, 2.7 mmol, 1.0 eq) was added thereto dropwise. Then, the mixture was warmed to room temperature, and heated to reflux overnight. TLC confirmed that there was still some starting material in the reaction liquid. The reaction liquid was cooled to 0° C., and concentrated sulfuric acid (530 mg, 5.4 mmol, 2.0 eq) was added thereto, and then heated to reflux for 8 hours. The reaction was completed which was confirmed by TLC. The reaction liquid was cooled to room temperature, poured into about 50 ml of ice water, stirred for 20 minutes, filtered, and the filter cake was rinsed with water. The resultant was dried to give compound 12-2 as yellow solid (504 mg, yield 94%), which was directly used in the next reaction.

Lithium aluminum hydride (374 mg, 12.48 mmol, 1.5 eq) was suspended in dry THF (5.0 ml), protected with nitrogen, cooled to −30° C. overnight. Methyl thieno [3,2-B]thiophene-2-carboxylate (1.65 g, 8.32 mmol, 1.0 eq) was dissolved in THF (10 ml), and the obtained solution was slowly added dropwise to the above lithium aluminum hydride solution. After the addition was finished, the temperature was gradually raised to room temperature in 1 hour. TLC monitored the reaction until the reaction was completed. The reaction system was cooled to −20° C. and then EA was added dropwise until no significant bubbles were formed. Then, 20% aqueous sodium hydroxide solution was added dropwise to form a loose precipitate. The resultant was filtered, and the filter cake was rinsed with EA. The filtrate was washed with aqueous saturated ammonium chloride solution twice, washed with water once, brine once, dried over anhydrous sodium sulfate and filtrated. The filtrate was concentrated to give dry crude. The crude product was slurried in n-hexane (15 ml) for 30 minutes. Then, the mixture was filtered and the filter cake was concentrated under reduced pressure to give dry compound 12-3 (1.29 g, yield, 90.8%).

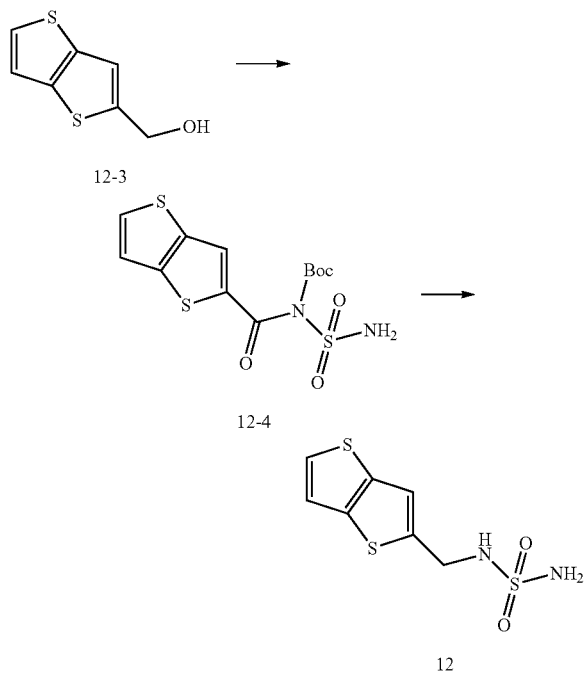

Thieno[3,2-b]thiophen-2-methanol (compound 12-3) (366 mg, 2.15 mmol, 1.0 eq) and BSA 422 mg (2.15 mmol, 1.0 eq) were dissolved in dry THF (7.5 ml). Triphenylphosphine (620 mg, 2.37 mmol, 1.1 eq) was added thereto under nitrogen environment, and the mixture was cooled to −10° C. with ice-salt bath. Then, diethyl azodicarboxylate (DEAD) (412 mg, 2.37 mmol, 1.1 eq) was added while keeping the temperature below 0° C. After the addition was finished, the mixture was warmed to room temperature and reacted overnight. TLC confirmed that there was still small amount of staring materials in the reaction liquid. The reaction liquid was concentrated to dryness, and the residue was dissolved in dichloromethane, and purified by column chromatography (eluent petroleum ether/ethyl acetate=100/1 to 5/1). The product was collected and concentrated to dry to give compound 12-4 as white solid (331 mg, yield of 44.2%).

The compound 12-4 (331 mg) obtained in the previous step was dissolved in methanol (10 ml), cooled to 0° C. in an ice bath. And then, hydrogen chloride in ethanol (3.2 ml) was added, and the mixture was stirred at room temperature overnight. TLC confirmed the reaction was completed. The resultant was concentrated to dryness under reduced pressure, and purified by column chromatography (eluent petroleum ether/ethyl acetate=100/1 to 5/1). The product was collected and concentrated to give the pure compound 12 (176 mg) as an off-white solid with yield of 74.5%.

$^1$H NMR (DMSO-d$_6$) δ: 7.60 (d, 1H), 7.40 (d, 1H), 7.35 (s, 1H), 7.27 (t, 1H), 6.71 (s, 2H), 4.31 (d, 2H);

ESI-MS m/z: 248.91 (M+1).

Example 13:
N-[(2-chloro-3-thienyl)methyl]-sulfamide

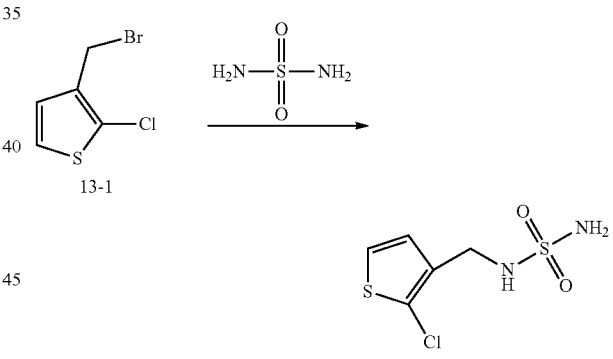

Aminosulfonamide (1.363 g, 14.18 mmol, 3.0 eq) was dissolved in DMF (15 ml), potassium carbonate (783 mg, 5.67 mmol, 1.2 eq) was added thereto and the mixture was cooled to 0° C. 2-chloro-3-bromomethyl thiophene (compound 13-1) 1.0 g (4.73 mmol, 1.0 eq) was added thereto and the reaction liquid was stirred at room temperature overnight. The reaction was monitored by TLC until the reaction was completed. The reaction solution was poured into ice water (100 ml), extracted with ethyl acetate twice. The combined organic phase was washed with water once and saturated brine once, dried over anhydrous sodium sulfate, and filtered. The filtrate was concentrated to give dry crude product. The crude product was purified by column chromatography (eluent petroleum ether/ethyl acetate=100/1 to 3/1). The product was collected and concentrated to give compound 13 (324 mg) as a pale yellow solid with yield of 32%.

$^1$H NMR (DMSO-d$_6$) δ: 7.40 (d, 1H), 7.08-7.03 (m, 2H), 6.66 (s, 2H), 3.98 (d, 2H);
ESI-MS m/z: 224.98 (M−1), 227.02 (M+2−1).

Example 14: Benzo[d]isothiazol-3-ylmethyl Sulfamate

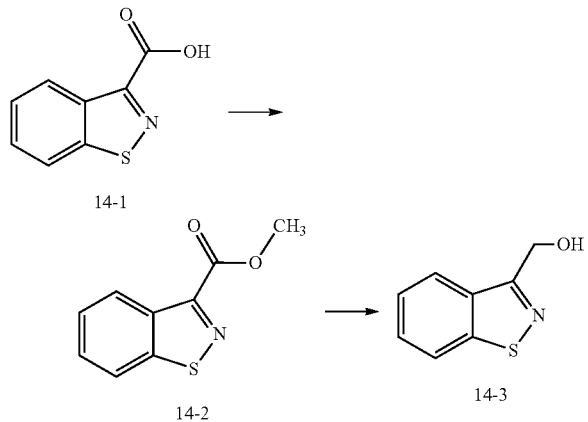

Compound 14-1 (3 g) was dissolved in methanol (60 ml), and the mixture was cooled to 0° C. Then thionyl chloride (6 mL) was added dropwise to the reaction liquid. The reaction liquid was heated to reflux. After the reaction was completed, the reaction liquid was cooled to room temperature. The solvent was removed by concentration and the residue was dissolved in ethyl acetate (60 mL) and washed with water. The organic layer was dried and concentrated under reduced pressure to give the product compound 14-2 (3 g).

Compound 14-2 (1.2 g) was dissolved in THF (60 ml) and then the mixture was cooled to 0° C., LiBH$_4$ (0.23 g) was added to the reaction solution. After the reaction liquid was stirred for 1 hour, a saturated NaHCO$_3$ solution was added dropwise thereto. The resultant was extracted with ethyl acetate (50 mL×2) to separate organic layer which was dried, and concentrated under reduced pressure to give compound 14-3 (0.8 g).

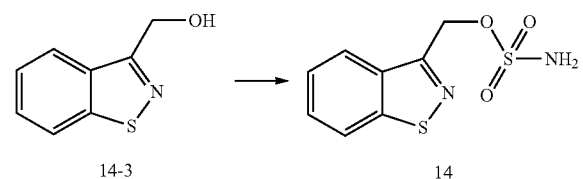 [SMILES: OCc1nsc2ccccc12 ; NS(=O)(=O)OCc1nsc2ccccc12]

Compound 14-3 (0.5 g) was dissolved in DMA (5 mL) and aminosulfonyl chloride (1 g) was added to the reaction liquid and stirred at room temperature for 10-12 hours. After the completion of the reaction was confirmed by TLC, water (20 mL) and ethyl acetate (50 mL) were added to the reaction system. The organic layer was separated, dried, concentrated under reduced pressure and subjected to column chromatography to give compound 14 (0.2 g).

$^1$H NMR (DMSO-d$_6$) δ: 8.28 (d, 1H), 8.21 (d, 1H), 7.84 (s, 2H), 7.68 (td, 1H), 7.59 (td, 1H), 5.49 (s, 2H);
ESI-MS m/z: 243.0 (M−1).

The Maximal Electroshock Seizure Test on Mice

MES (maximal electroshock seizure test) was used to evaluate whether the compounds have an effect against IVIES and thus to make preliminary evaluation of the efficacy of each compound in treating epilepsy. Multipurpose instrument for pharmacological and biological experiments (mode, YSD-4G) was used to conduct experiments under the condition of convulsive mode, 115V of stimulation voltage, 250 ms of stimulation time, 50 HZ AC voltage. Positive and negative electrodes were used to clamp the left and right ear of the mice, respectively, which were wetted by normal saline. The tonic hind limb extension seizure after stimulation was deemed as judgment standard of grand mal. The mice were randomly divided into groups. The compounds were given by intragastric administration based on the dose of 100 mg/kg. The effect of the compound on IVIES was observed at 0.5 h, 1.5 h and 2 h after administration. The results were shown in table 1.

TABLE 1

Antiepileptic effect of the compounds

| Testing time | Inhibition rate of epileptic seizure* | | |
|---|---|---|---|
| | 0.5 h | 1.5 h | 2 h |
| Topiramate | 37.5% | 37.5% | |
| Zonisamide | 33.3% | 16.7% | 16.7% |
| JNJ-26990990 | 20% (literature value) | | 60% (literature value) |
| Compound of Example 1 | 66.7% | | 50% |
| Compound of Example 2 | | | 33.3% |
| Compound of Example 3 | 88.9% | 66.7% | 77.8% |
| Compound of Example 9 | 44.4% | | 11.1% |
| Compound of Example 13 | 37.5% | | |

*Inhibition rate of epileptic seizure: the number of mice with generalized tonic-clonic seizures/the total amount of the mice involved in the experiments

Study on the Influence of the Compounds on the Rats' Total Cholesterol and Triglyceride 50 male SD rats with weight of 180~200 g were randomly divided into groups with 8 in each group. The vehicle control, topiramate (40 mg/kg) and the compound of Example 3 in dose of 20 mg/kg, 40 mg/kg, 80 mg/kg were given by intragastric administration. 5 weeks after administration, the level of total cholesterol and triglyceride in rats' serum were determined and the results were shown in table 2. The results showed that the compound of Example 3 can significantly decrease the level of total cholesterol and triglyceride.

TABLE 2

Testing results of the level of total cholesterol and triglyceride in rats' serum

| Group | dose (mg/kg) | total cholesterol | triglyceride |
|---|---|---|---|
| Vehicle control | — | 1.57 ± 0.14 | 1.42 ± 0.2 |
| Topiramate | 40 | 1.56 ± 0.19 | 1.45 ± 0.34 |
| Compound of Example 3 | 20 | 1.64 ± 0.28 | 1.13 ± 0.24* |
| Compound of Example 3 | 40 | 1.53 ± 0.17 | 0.99 ± 0.16** |
| Compound of Example 3 | 80 | 1.32 ± 0.21* | 0.84 ± 0.06** | note:
*<0.05;
**<0.01

Inhibiting Effect of the Compounds on Carbonic Anhydrase

The testing method for testing the inhibiting effect of the compounds on carbonic anhydrase was conducted with reference to literature (Chem Biol Drug Des 2006 68: 113-119), Human carbonic anhydrase II (CA-II), HEPES and Tri were purchased from Sigma.

Preparation Method of the Reagent

Chromogenic Buffer Solution:

HEPES was dissolved in distilled water to prepare a solution with a concentration of 10 mM; the pH was adjusted to 7.7 with 1 M Tris at 23° C.; bromothymol blue was dissolved in HEPES buffer solution with pH 7.7 to a concentration of 50 mg/L;

Saturated $CO_2$-ice water was prepared by adding dry ice into icy distilled water.

Solution of CA-II enzyme was prepared into a concentration of 2 m/ml, and stored at −20° C.

Tested sample was prepared by using distilled water as solvent with various concentrations.

Test Steps:

| Item | blank tube | standard tube | test tube |
| --- | --- | --- | --- |
| chromogenic buffer solution | 0.5 ml | 0.5 ml | 0.5 ml |
| freshly prepared solution of enzyme | | 0.1 ml | 0.1 ml |
| distilled water | 0.2 ml | 0.1 ml | |
| test compound | | | 0.1 ml |
| mixing, ice bath for 15 min | | | |
| saturated $CO_2$-ice water | 0.3 ml | 0.3 ml | 0.3 ml |
| ice bath, mixing slowly, shaking every 15-30 s until it became yellow | | | |

The time required for changing into yellow was recorded. The time required for the blank tube was recorded as $t_0$, the time required for the standard tube was recorded as $t_s$ and the time required for the test tube was recorded as t. $(t_0-t_s)/t_s$ was normal activity of enzyme, and $(t_0-t)/t$ was the activity after affecting by the test compound.

Test Results

The $IC_{50}$ of the compound of Example 3 on the carbonic anhydrase was 154 μM, the $IC_{50}$ of the topiramate on the carbonic anhydrase inhibitory activity was 0.89 μM, and the $IC_{50}$ of the zonisamide on the carbonic anhydrase was 14.7 μM. The compound of Example 3 has poorer inhibiting effect than topiramate and zonisamide.

What is claimed is:

1. An aminosulfonyl-based compound represented by formula I or a tautomer, enantiomer, racemate or pharmaceutically acceptable salt thereof,

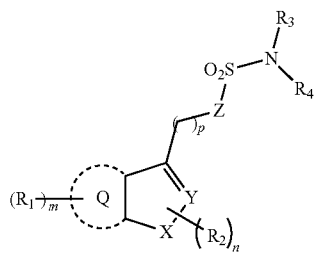

I wherein

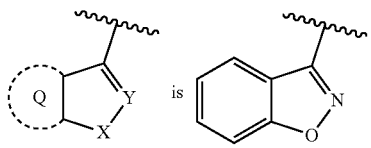

Z is N—$R_5$, O or $CHR_5$; when X is O and Y is N, Z is not O or $CH_2$;

m is an integer of 0 to 4;

n is a integer of 0 to 2;

p is an integer of 1 to 2;

$R_1$s are each independently hydrogen, amino, halogen, trifluoromethyl, hydroxyl, nitro, nitrile, mercapto, carboxyl, aldehyde group, oxo(=O) group, thio(=S) group, C1~C10 alkyl, C2~C10 alkenyl, C2~C10 alkynyl, C3~C10 cycloalkyl, C1~C10 alkoxyl, C1~C10 alkylacyl, C1~C10 alkoxyl carbonyl, C1~C10 alkylacyloxy, —$NR_6R_7$, —$CONR_6R_7$, —$OCONR_6R_7$, C1~C10 thioalkyl, sulfonic acid group, aminoformyl, sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S;

wherein the amino, C1~C10 alkoxy, C1~C10 alkyl, C1~C10 alkyl acyl, C1~C10 alkoxyl carbonyl, C1~C10 alkyl acyloxy, sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S may be optionally substituted by one or more substituents selected from a group consisting of halogen, trifluoromethyl, hydroxyl, nitro, amino, cyano, carboxyl, aldehyde group, C1~C10 alkyl, C1~C10 alkoxyl, C1~C10 alkylacyloxy, C1~C10 alkoxyl carbonyl, C1~C10 alkyl acyl, sulfonyl, C1~C10 alkyl sufonyl, phenyl, and benzyl;

$R_2$s are each independently hydrogen, amino, halogen, trifluoromethyl, hydroxyl, nitro, cyano, mercapto group, carboxyl, aldehyde group, C1~C10 alkyl, C2~C10 alkenyl, C2~C10 alkynyl, C3~C10 cycloalkyl, C1~C10 alkoxyl, C1~C10 alkyl acyl, C1~C10 alkoxylcarbonyl, C1~C10 alkyl acyloxy, —$NR_6R_7$, —$CONR_6R_7$, —$OCONR_6R_7$, C1~C10 thioalkyl, sulfonic acid group, amino formyl, sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S;

wherein the amino, C1~C10 alkoxy, C1~C10 alkyl, C1~C10 alkyl acyl, C1~C10 alkoxyl carbonyl, C1~C10 alkyl acyloxy, sulfonyl, C6~C10 aryl, 4-~10-membered heterocyclic group or 4-~10-membered heteroaryl may be optionally substituted by one or more substituents selected from a group consisting of halogen, trifluoromethyl, hydroxyl, nitro, amino, cyano, carboxyl, aldehyde group, C1~C10 alkyl, C1~C10 alkoxyl, C1~C10 alkyl acyloxy, C1~C10 alkoyxl carbonyl, C1~C10 alkyl acyl, sulfonyl, C1~C10 alkyl sulfonyl, phenyl, and benzyl;

$R_3$ and $R_4$ are each independently hydrogen, amino, trofluoromethyl, hydroxyl, carboxyl, aldehyde group, amino, C1~C10 alkyl, C2~C10 alkenyl, C2~C10 alkynyl, C3~C10 cycloakyl, C1~C10 alkoxyl, C1~C10 alkoxyl carbonyl, C1~C10 alkyl acyl, C1~C10 alkyl acyloxy, sulfonyl, C6~C10 aryl, 4-~10-membered heterocyclic group containing 1~4 heteroatoms selected from a group consisting of N, O and S, or 4-~10-membered heteroaryl containing 1~4 heteroatoms selected from a group consisting of N, O and S;

wherein the amino, C1~C10 alkyl, C1~C10 alkoxy, C1~C10 alkoxyl carbonyl, C1~C10 alkyl acyl, C1~C10 alkyl acyloxy, sulfonyl, C6~C10 aryl, 4-~10-membered heterocyclic group containing 1 to 4 heteroatoms selected from a group consisting of N, O and S, or 4-~10-membered heteroaryl containing 1 to 4 heteroatoms selected from a group consisting of N, O and S may be optionally substituted by one or more substituents selected from a group consisting of halogen, trifluoromethyl, hydroxyl, nitro, amino, cyano, carboxyl, aldehyde group, C1~C10 alkyl, C1~C10 alkoxyl, C1~C10 alkyl acyloxy, C1~C10 alkoxyl carbonyl, C1~C10 alkyl acyl, sulfonyl, C1~C10 alkyl sulfonyl, phenyl and benzyl;

or $R_3$ and $R_4$ together with the N atom to which they are bonded form a 4- to 8-membered heterocyclic group or 4- to 8-membered heteroaryl containing 1 to 4 heteroatoms selected from a group consisting of N, S and O;

$R_5$ is H or C1~C10 alkyl; and $R_6$ and $R_7$ are each independently H or C1~C10 alkyl, or $R_6$ and $R_7$ together with the N atom to which they are bonded form a 4-~8-membered heterocyclic group containing 1~4 heteroatoms selected from a group consisting of N, S and O, or form 4-~8-membered heteroaryl containing 1~4 heteroatoms selected from a group consisting of N, S and O.

2. The aminosulfonyl-based compound represented by formula I or a tautomer, enantiomer, racemate or a pharmaceutically acceptable salt thereof according to claim 1, wherein, Z is N—$R_5$;
m is 0, 1 or 2;
n is 0 or 1;
p is 1;
$R_1$s are each independently hydrogen, halogen, trifluoromethyl, hydroxyl, nitro, cyano, mercapto, carboxyl, aldehyde group, C1~C8 alkyl, C2~C8 alkenyl, C2~C8 alkynyl, C3~C8 cycloakyl, C1~C8 alkoxyl, C1~C8 alkyl acyl, C1~C8 alkoxy carbonyl, C1~C8 alkyl acyloxy, —NR$_6$R$_7$, —CONR$_6$R$_7$, —OCONR$_6$R$_7$, C1~C8 thioalkyl, sulfonamido, aminoformyl, sulfonyl, C1~C8 alkylsulfonyl, C6~C10 aryl, 4-~10-membered heterocyclic group or 4-~10-membered heteroaryl containing 1~3 heteroatoms selected from a group consisting of N, O and S;

$R_2$s are each independently hydrogen, halogen, trifluoromethyl, hydroxyl, nitro, cyano, amino, mercapto, carboxyl, aldehyde group, C1~C8 alkyl, C2~C8 alkenyl, C2~C8 alkynyl, C3~C8 cycloakyl, C1~C8 alkoxyl, C1~C8 alkyl acyl, C1~C8 alkoxy carbonyl, C1~C8 alkyl acyloxy, —NR$_6$R$_7$, —CONR$_6$R$_7$, —OCONR$_6$R$_7$, C1~C8 thioalkyl, sulfonic acid group, sulfonamido, aminoformyl, sulfonyl, C1~C8 alkylsulfonyl, C6~C10 aryl, 4-~10-membered heterocyclic group containing 1~3 heteroatoms selected from a group consisting of N, O and S, or 4-~10-membered heteroaryl containing 1~3 heteroatoms selected from a group consisting of N, O and S;

$R_3$ and $R_4$ are each independently H or C1~C8 alkyl or 5-~6-membered heteroaryl;

or $R_3$ and $R_4$ together with the N atom to which they are bonded form a 5- to 7-membered heterocyclic group containing 1 to 3 heteroatoms selected from a group consisting of N, S and O or 5- to 7-membered heteroaryl containing 1 to 3 heteroatoms selected from a group consisting of N, S and O;

$R_5$ is H or C1~C3 alkyl;

$R_6$ and $R_7$ are each independently H or C1~C8 alkyl;

or $R_6$ and $R_7$ together with the N atom to which they are bonded form a 5- to 7-membered heterocyclic group or 5- to 7-membered heteroaryl containing 1 to 3 heteroatoms selected from a group consisting of N, S and O.

3. The aminosulfonyl-based compound represented by formula I or a tautomer, enantiomer, racemate or a pharmaceutically acceptable salt thereof according to claim 1, wherein, Z is N—$R_5$;
m is 0, 1 or 2;
n is 0 or 1;
p is 1;
$R_1$ is H, F, Cl, NO$_2$, NH$_2$, NHCOCH$_3$ or methoxyl;
$R_2$ is H or methyl;
$R_3$ and $R_4$ are each independently H, methyl, ethyl, or imidazolyl;
$R_5$ is H;
$R_6$ and $R_7$ are each independently H or methyl.

4. The aminosulfonyl-based compound represented by formula I or a tautomer, enantiomer, racemate or a pharmaceutically acceptable salt thereof according to claim 1, wherein, the aminosulfonyl-based compound is selected from the group consisting of:

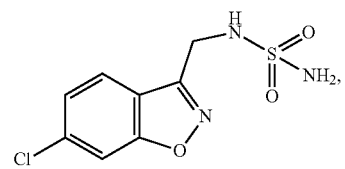

1

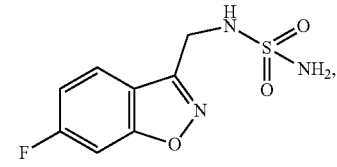

2

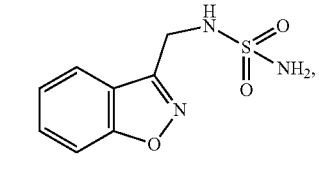

3

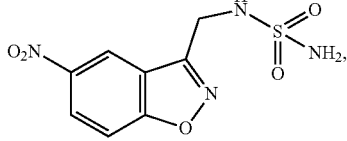

5

-continued

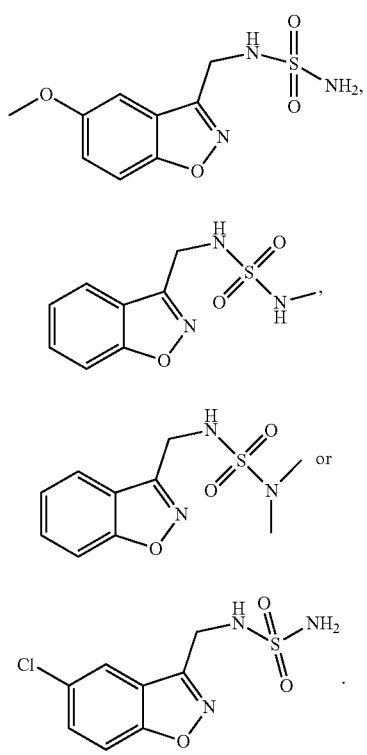

5. A method for preparing an aminosulfonyl-based compound represented by formula I, wherein the aminosulfonyl-based compound is prepared by the one of the following methods:

(1) when Z is NH, 1) compounds I-2 are prepared by sulfonylation between bromide II and aminosulfonamide compound VI which is protected by protecting groups, deprotection, and amination reaction:

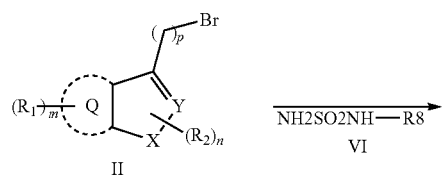

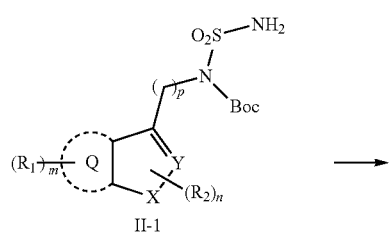

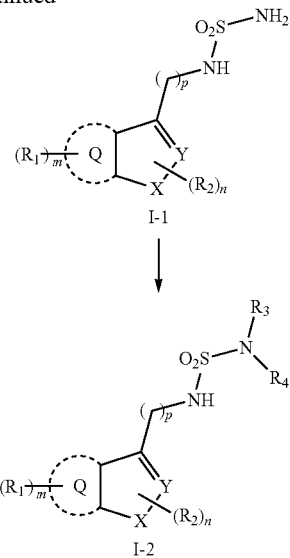

wherein compound II and compound VI are subjected to sulfonylation in the presence of a base to give compound II-1, wherein R8 is a Boc group
removed in acidic condition;
the amination reaction is carried out by the amination reaction of $R_3$-A, $R_4$-A or A-$R_3$-$R_4$—B with compound I-1 in the presence of a base, wherein A and B are the same or different, and are each independently Cl, Br or I;

or 2) compound I-2 is prepared by sulfonylation between bromide compound III and aminosulfonamide compound VII which is protected by protecting groups, deprotection, and amination reaction:

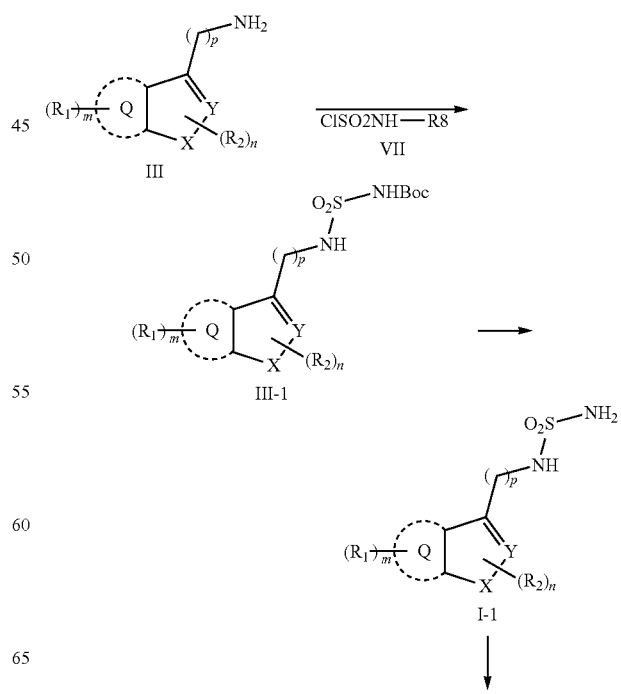

-continued

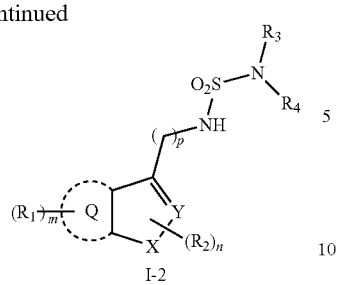

I-2 wherein compound III and compound VII are subjected to sulfonylation in the presence of a base catalyst to give compound III-1, wherein R8 is a Boc group;
compound III-1 is subjected to deprotection reaction under acidic condition to give compound I-1;
haloalkanes $R_3$-A, $R_4$-A or A-$R_3$-$R_4$—B and compound I-1 are subjected to amination in the presence of alkali to give compound I-2, wherein A and B are the same or different, and are each independently Cl, Br or I;

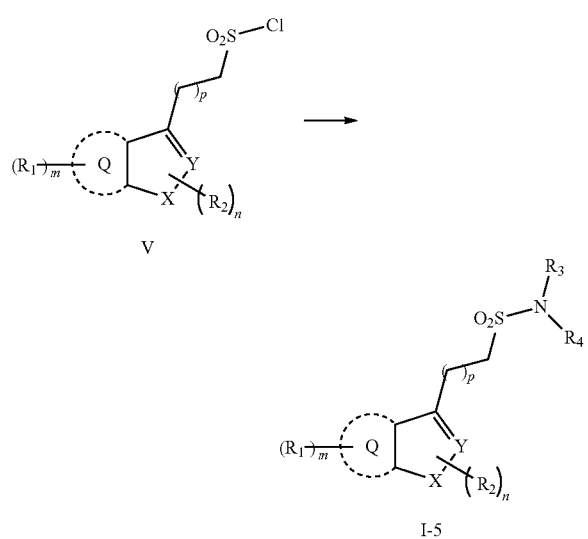

compound V and amine $HNR_3R_4$ are subjected to amination to give compound I-5;

(2) when Z is N—$R_5$ or CH—$R_5$, the compound represented by formula I is prepared from a compound represented by formula I-2 or formula I-5 by an alkylation reaction, wherein the compound represented by formula I-5 is obtained by reacting compound V and $HN_3R_4$ through amination,

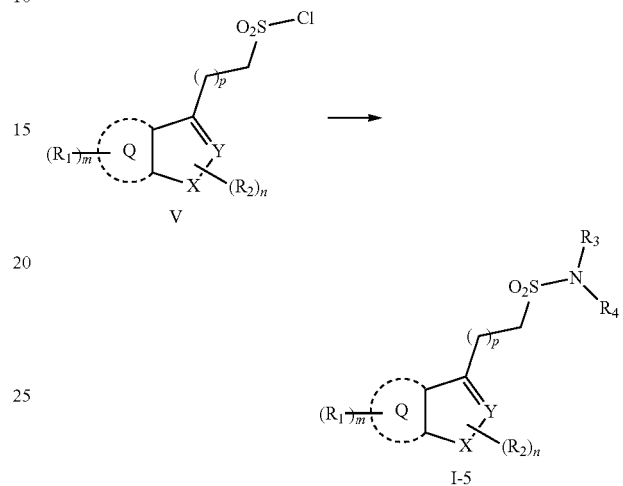

wherein, X, Y, Q ring, m, n, p, $R_1$ and $R_2$ are defined same as in claim 1; $R_3$ and $R_4$ are defined same as in claim 1 except they are not hydrogen; $R_5$ is C1-C10 alkyl.

6. A pharmaceutical composition comprising a therapeutically effective amount of a compound or a tautomer, enantiomer, racemate or pharmaceutically acceptable salt thereof according to claim 1, and a pharmaceutically acceptable carrier.

7. A method for treating epilepsy, convulsions or obesity, comprising:
administering an effective amount of a compound or a tautomer, enantiomer, racemate or pharmaceutically acceptable salt thereof according to claim 1 to a subject in need of such treatment.

* * * * *